United States Patent [19]
Foster et al.

[11] Patent Number: 5,337,845
[45] Date of Patent: Aug. 16, 1994

[54] VENTILATOR, CARE CART AND MOTORIZED TRANSPORT EACH CAPABLE OF NESTING WITHIN AND DOCKING WITH A HOSPITAL BED BASE

[75] Inventors: L. Dale Foster; Ryan A. Reeder, both of Brookville, Ind.

[73] Assignee: Hill-Rom Company, Inc., Batesville, Ind.

[21] Appl. No.: 7,122

[22] Filed: Jan. 21, 1993

Related U.S. Application Data

[63] Continuation-in-part of Ser. No. 912,826, Jul. 13, 1992, which is a continuation-in-part of Ser. No. 874,586, Apr. 24, 1992, which is a continuation-in-part of Ser. No. 524,038, May 16, 1990, Pat. No. 5,117,521.

[51] Int. Cl.$^5$ .............................. B62M 27/02
[52] U.S. Cl. ........................ 180/11; 180/13; 180/19.1; 180/65.1; 5/510
[58] Field of Search ............ 180/11, 12, 13, 16, 180/19.1, 19.3, 65.1, 65.8, 907; 5/118, 119, 510, 600

[56] References Cited

U.S. PATENT DOCUMENTS

| | | | |
|---|---|---|---|
| 2,039,901 | 5/1936 | Hawley | 312/209 |
| 2,607,929 | 8/1952 | Balluff | 5/618 |
| 2,847,006 | 8/1958 | Griffith | 128/202.13 |
| 2,978,053 | 4/1961 | Schmidt | 180/16 |
| 3,281,103 | 10/1966 | Kisling | 248/132 |
| 3,524,512 | 8/1970 | Voeks et al. | 180/14.1 |
| 3,876,024 | 4/1975 | Shieman et al. | 180/19.1 |
| 4,578,833 | 4/1986 | Vrzalik | 5/607 |
| 4,584,989 | 4/1986 | Stith | 600/18 |
| 4,768,241 | 9/1988 | Beney | 5/600 |
| 4,894,876 | 1/1990 | Fenwick | 5/602 |
| 4,944,292 | 7/1990 | Gaeke | 128/204.18 |
| 4,945,592 | 8/1990 | Sims | 5/658 |
| 4,953,243 | 9/1990 | Birkmann | 5/600 |
| 4,957,121 | 9/1990 | Icenogle | 128/897 |
| 4,966,340 | 10/1990 | Hunter | 248/125 |
| 4,985,946 | 1/1991 | Foster et al. | 5/601 |
| 5,022,105 | 6/1991 | Catoe | 5/11 |
| 5,042,470 | 8/1991 | Kanesaka | 128/202.22 |
| 5,050,695 | 9/1991 | Kleinwolterink | 180/13 |
| 5,054,141 | 10/1991 | Foster et al. | 5/611 |
| 5,072,906 | 12/1991 | Foster | 248/122 |
| 5,083,625 | 1/1992 | Bleicher | 180/65.1 |
| 5,117,521 | 6/1992 | Foster et al. | 5/510 |
| 5,117,819 | 6/1992 | Servidio | 128/204.18 |

FOREIGN PATENT DOCUMENTS

| | | |
|---|---|---|
| 2818189 | 6/1979 | Fed. Rep. of Germany . |
| 2812037 | 9/1979 | Fed. Rep. of Germany . |
| 2285113 | 4/1976 | France . |
| 2153771 | 8/1985 | United Kingdom . |

*Primary Examiner*—Brian L. Johnson
*Assistant Examiner*—Kevin Hurley
*Attorney, Agent, or Firm*—Wood, Herron & Evans

[57] ABSTRACT

Apparatus for motorized transport of the hospital bed and care cart docks to the head end of the bed and has a drive wheel, a motor propelling the drive wheel, a joy stick type potentiometer for controlling the speed and direction of the drive wheel and handles for grasping the apparatus and maneuvering the apparatus and the hospital bed. Gas springs are actuated by the bed when the motorized transport apparatus and bed are docked together for exerting a downward force on the drive wheel to reduce the tendency of the drive wheel to slip. The apparatus falls within the footprint of the bed.

45 Claims, 14 Drawing Sheets

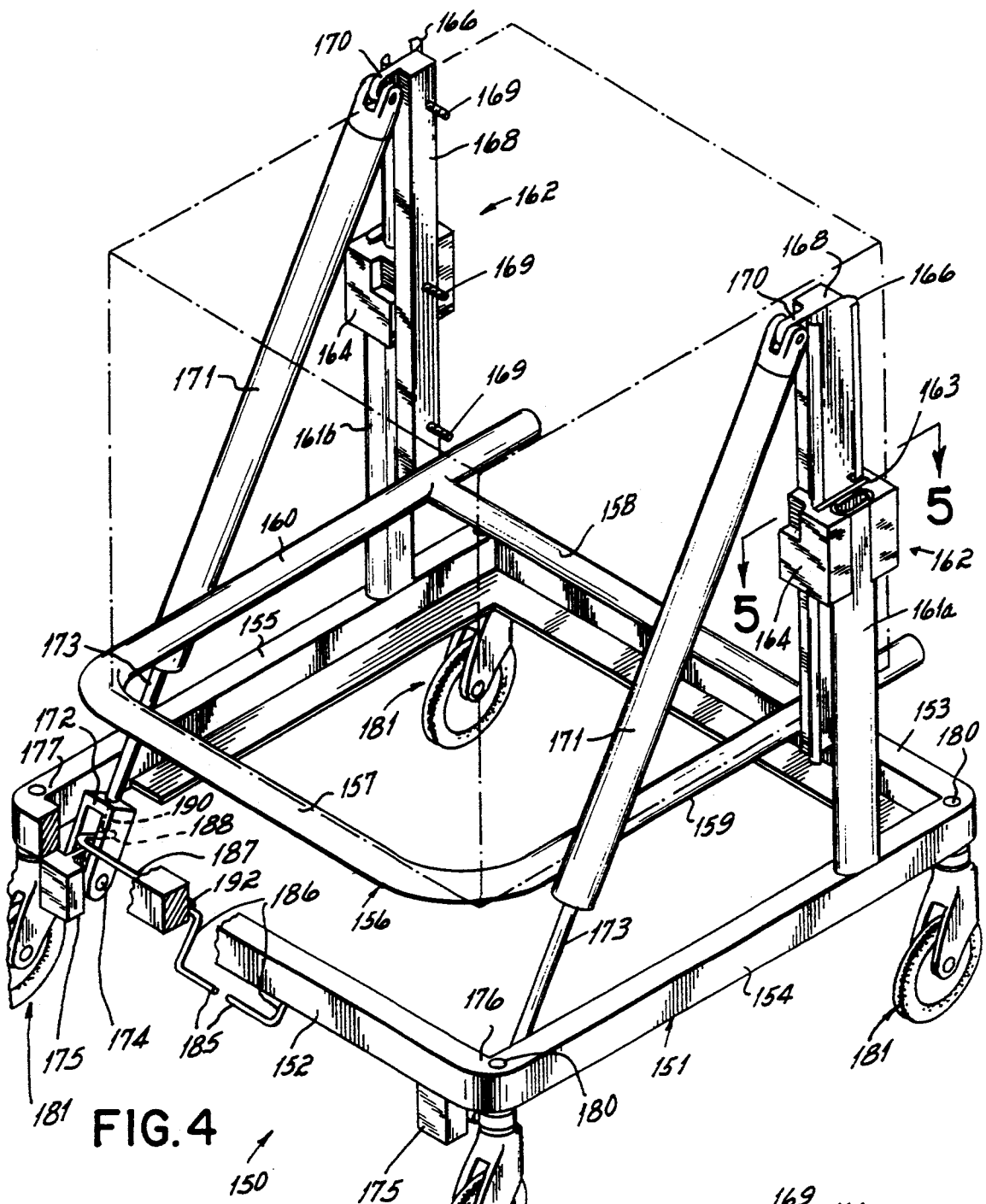

VENTILATOR, CARE CART AND MOTORIZED TRANSPORT EACH CAPABLE OF NESTING WITHIN AND DOCKING WITH A HOSPITAL BED BASE

RELATED APPLICATIONS

This application is a continuation-in-part of our co-pending application Ser. No. 07/912,826 filed Jul. 13, 1992, which is a continuation-in-part of our co-pending application Ser. No. 07/874,586 filed Apr. 24, 1992 which is a continuation-in-part of our co-pending application Ser. No. 07/524,038 entitled Care Cart and Transport System filed May 16, 1990, now U.S. Pat. No. 5,117,521 having issued Jun. 2, 1992.

FIELD OF THE INVENTION

This invention relates generally to medical equipment, and more particularly to the integration of patient life support systems into the dimensions of a hospital bed. More specifically, this invention relates to patient ventilators and carts for supporting ventilators, and care carts for supplying patient ventilators with DC electricity, oxygen and air, in combination with hospital beds for movement with the beds. Additionally, this invention relates to motorized transport of hospital beds and care carts in combination with hospital beds.

BACKGROUND OF THE INVENTION

The patient critical care environment in hospitals is becoming increasingly crowded due to the number of pieces of medical equipment associated with critical care, which pieces of equipment embody various critical care technologies. Specifically, within the critical care environment there is generally located a critical care bed, around which are positioned a ventilator, I.V. pumps, various monitors, and one or more computer terminals for entering patient care data. The numerosity of pieces of equipment spaced about a critical care hospital room and the patient bed results in patient care inefficiency, as a care provider must continually monitor and operate all the pieces of equipment, while such are not advantageously ergonomically arranged.

In addition to the critical care environment being crowded and somewhat cumbersome around which to work, the transfer of the various pieces of equipment along with the patient on the critical care bed from one room to another within the hospital is tedious, time consuming and difficult to manage. One reason is that the critical care bed, and the various technologies associated with the critical care environment, are generally each individually supported on wheeled support structures. Therefore, when transferring the patient from one room to another room, several pieces of wheeled equipment must simultaneously be rolled to the new location. Not only is this task cumbersome, but also it is time consuming. Further, since all the various technologies must be first disconnected from their respective connections to AC power at the wall in the room, the various technologies must either operate on some sort of standby scheme during transportation, or must be manually operated. Swift transfer of the various pieces of equipment with the critical care bed from one room to another is mandatory in order to minimize down time on these pieces of equipment yet is made very difficult by the clutter associated with the several individual pieces of equipment.

Use of a ventilator in a critical care context normally requires the use of one or more oxygen and air canisters or bottles, to supply the ventilator with air and oxygen. These bottles are normally placed beside a critical care bed for supplying the ventilator with oxygen and air while the patient is hooked up to the ventilator. During transport of the patient on the bed, with the patient still hooked up to the ventilator, transport of the air and oxygen bottles along with patient, bed and ventilator has presented a problem. One solution which has proved to be unsatisfactory is to simply place the oxygen and air bottles in the bed with the patient for transport with the patient. Such a solution has obvious drawbacks, such as decreasing the effective amount of bed space available for the patient, increasing the likelihood of patient injury upon contacting the bottles and increasing the likelihood of patient care provider injury upon lifting and placing the bottles into the bed.

In a critical care environment the patient can be invasively and/or non-invasively connected to dozens of devices, for example, IV pumps, drainage devices, vital signs monitoring, ventilator and pressure transducers. Doctors often require diagnostic imaging such as x-ray, CT scan, MRI, PET scans, nuclear imaging, and/or invasive procedures such as angiogram, cath lab, and surgery performed upon these patients. These procedures cannot be performed in the patient room, and therefore the patient and all of his or her ancillary devices must be taken to the procedure. In order to transport the critically ill patient and his or her life support devices ancillary items, for example, drug box, oxygen bottles, defibrillator, and transport monitor, must be taken along to support the devices and as emergency precautions. In order to transport all of these devices and items as well as the patient as many as six attendants, including nurses, respiratory therapists, doctors, residents, and transport personnel may be required. And before transport, the aforementioned ancillary equipment items such as drug box, oxygen tanks, ambu bag, portable ventilator, defibrillator, transport monitor, portable suction, IV stands, and the like, which are not kept in the patient room, must be gathered. These items can be stored in several separate locations and may also be misplaced and difficult to locate. Therefore, the gathering, managing and transporting of the aforementioned items has in the past created much difficulty, taxing numerous care providers and expending critical time.

SUMMARY OF THE INVENTION

In accordance with the principles of this invention, a significant improvement in patient critical care and movement is made by consolidating the patient ventilator required in a typical critical care environment not only for its stationary use but also for transportation purposes as well. That is, rather than rolling the patient ventilator along with the patient bed from one room to the next, the present invention enables a hospital worker to roll, as a single unit, both the bed and the ventilator as a single, integrated critical care unit.

The typical critical care bed is manufactured to certain external dimensions to enable the bed to be rolled, for example, through doorways, down aisles, and into elevators. The external dimensions of the bed are referred to as the bed's "footprint". Hospital workers are familiar with maneuvering such a standard critical care bed within this footprint. The present invention combines movement of the ventilator with the critical care bed within this footprint in such a manner that the outer dimensions of the critical care bed are not exceeded, thereby taking advantage of the fact that the bed has been designed to freely travel down aisles, through doors and the like, and of the familiarity of the hospital worker with maneuvering the critical care bed.

The patient ventilator which normally stands in a position next to the bed is in accordance with this invention capable of being quickly and efficiently locked within the patient bed base and within the bed footprint for rolling movement with the bed from one location to another.

Since the ventilator must be disconnected from its source of AC power at the hospital room wall before transferring it to a new room, this invention provides for powering the ventilator directly by the bed itself. This eliminates any down time of the ventilator thereby providing for uninterrupted operation of the ventilator during movement of the patient and patient bed.

The present invention provides a hospital bed supported on a wheeled base, and a ventilator supported on a wheeled cart which may be docked to the base of the bed, the combination of ventilator and bed capable of being rolled as a single unit within the bed footprint.

The ventilator cart of the present invention includes a wheeled base, and supports connected to the base for supporting a ventilator, with the supports providing for selective raising and lowering of a ventilator supported by the supports. The ventilator cart provides for positioning the ventilator in a high position for operating the ventilator next to a patient bed and in a low position for docking the ventilator to the hospital bed base beneath a bed mounted on the base.

The hospital bed base is wheeled and has a generally Y-shaped base frame adapted to receive the wheeled ventilator cart in its lowered position such that the two may be docked together. The ventilator when docked within the outspread arms of the Y-shaped base frame of the hospital bed base falls within the footprint of the bed as projected downwardly onto the floor.

A mechanical latch is employed to secure the ventilator to the hospital bed base. The latch cooperates with a disabling switch which disables the high/low function of the bed mounted on the bed base, thereby preventing the bed from being lowered onto the ventilator. The disabling switch may be of the optical, mechanical or ribbon type. A power supply is mounted to the hospital bed base, and plugs into the ventilator when the ventilator is docked to the bed base, thereby providing for uninterrupted operation of the ventilator when transferring the ventilator from one room to another room.

The present invention also provides a hospital care cart which is adapted to dock to a foot end of the hospital bed for supplying DC electricity, oxygen and air to the ventilator when it is docked to the head end of the hospital bed. The care cart comprises a base having casters, a housing atop the base for housing batteries therein, a support extending upwardly from the base and adapted to support air and oxygen tanks, and structure for removably connecting the cart to the hospital bed base thereby permitting the cart and bed to be wheeled about as a unit. The support comprises a pair of vertically oriented posts extending upwardly from the rear of the base, a vertically oriented post extending upwardly from the front of the base, and a supporting platform connected between the posts for supporting two E size oxygen tanks and two E size air tanks. The supporting platform further includes a transversely oriented semicircular support structure mounted to an underneath side of the supporting platform for carrying a custom air tank. The care cart further includes a horizontally oriented shelf which projects forwardly from the upper ends of the pair of posts for supporting various items thereon during use of the cart, bed and ventilator, in a critical care environment.

Use of the care cart in conjunction with the hospital bed with ventilator docked thereto obviates the need for a separate power supply fixed to the bed. In that instance, the invention comprises the wheeled hospital bed having a head end and a foot end, a wheeled ventilator docked to and within a footprint of the bed at the head end, and a wheeled care cart adapted to supply the ventilator with DC electricity, oxygen and air docked to and within a footprint of the bed at its foot end, whereby the care cart supplies DC electricity, oxygen and air to the ventilator while the ventilator, bed and care cart are wheeled about as a single unit.

In addition to a DC power supply, an oxygen supply and an air supply, the care cart may be adapted to carry other additional items which would be useful in a critical care environment. For example, a drug box can be integrated into the shelf of the care cart. Further, a defibrillator can be mounted on the care cart. In addition, a transport monitor can be mounted on the care cart. Still further, a battery charger can be mounted on the care cart which would charge the batteries carried by the cart which power the ventilator. Still further, a portable suction can be mounted on the cart. Lastly, an air compressor can be mounted on the care cart which would charge the air tanks supported by the cart.

In another embodiment of the care cart, the care cart includes incorporated therewith a motorized pilot jack for motorized transport of the cart, bed and ventilator.

Another aspect of the present invention is the provision of a care cart which comprises a base with casters, a housing atop the base, a first support structure extending forwardly from the rear of the cart, and a second support structure extending forwardly from the rear of the cart and being spaced above the first support structure. The cart may be docked to the foot end of the hospital bed and within a footprint defined by the bed, as the second support structure is positioned above the foot section of the bed and the first support structure is positioned below the foot section of the bed when the cart is docked to the bed.

Still another feature of the present invention is the provision of a hospital bed which is capable of having a ventilator docked to its head end and a care cart docked to its foot end, the ventilator and care cart when docked to the bed being within the footprint defined by the bed. In this instance the hospital bed comprises the generally Y-shaped bed base having one end defining outspread arms and another end defining a stem, with the base having casters thereon, a patient support surface, and means supporting the patient support surface above the bed base. The outspread arms of the base are adapted to receive therein a wheeled ventilator, the ventilator when positioned therein being within a footprint of the patient's support surface defined by projecting downwardly onto to a floor surface therebelow the periphery of the support surface. The stem of the bed base is spaced inwardly a sufficient distance from the foot end of the bed to receive thereagainst a wheeled care cart, the cart when positioned thereagainst being within the footprint of the patient support surface.

A further aspect of the present is predicated upon the provision of apparatus for motorized transport of a hospital bed which has a generally Y-shaped castered base, one end of which has a pair of spaced arms. The apparatus comprises a castered base which is adapted to nest within the spaced arms of the Y-shaped hospital bed base and to dock thereto, a drive wheel on the base, a motor for powering the drive wheel, a joy stick-type potentiometer for controlling speed and direction of the drive wheel, and handles extending upwardly from the base for grasping the apparatus and maneuvering the apparatus and the hospital bed. The apparatus further includes gas springs which are actuated by the bed for exerting a downward force on the drive wheel to reduce a tendency of the drive wheel to slip on a floor surface. A latch is provided for latching the apparatus to the hospital bed. The apparatus when docked to the bed falls completely within the footprint of the bed.

The motorized transport device of the present invention is particularly useful when used in conjunction with a medical bed which has docked thereto the care cart of the present invention. In that case, the care cart would be removably docked to and within the footprint of the bed at one end, with the motorized transport being removably docked to and within the footprint of the bed at the other end. The care cart would provide life support to a patient situated atop the bed, and the motorized transport would assist the care provider in rolling the bed and care cart from place to place. In this form of the invention, the care cart would be adapted to support a miniaturized ventilator known as a "transport vent", along with the standard power supply, oxygen supply, and air supply. In this form of the invention, the mobile ventilator and its associated ventilator transport cart would be done away with. As in the prior embodiments of the care cart, it would be adapted to include a drug box, a defibrillator, a suction unit, a battery charger, and transport monitor, and in addition would be adapted to carry its own IV rack.

One advantage of the present invention is that transportation of a critical care bed and patient ventilator from one hospital room to another is facilitated. The docking of the ventilator to the bed base is quickly and easily accomplished thereby saving time when time may be critical to the patient.

Another advantage of the present invention is that the physical packaging associated with a critical care bed and its ventilator is reduced, as the ventilator has the ability to nest within and dock with a hospital bed base underneath and within the footprint of the bed and to move with the bed within its footprint.

Yet another advantage of the present invention is that a ventilator is able to operate in an uninterrupted manner when moving the ventilator with a bed from one hospital room to another hospital room.

Still another advantage of the present invention is that provision has been made for transporting oxygen and air tanks associated with a ventilator during transportation of a critical care bed and patient ventilator.

Still another advantage of the present invention is that the physical packaging associated with a critical care bed, its ventilator and its care cart is reduced, as the ventilator and care cart both have the ability to nest within and dock with a hospital bed base underneath and within the footprint of the bed.

A further advantage of the present invention is that a motorized transport is provided for assisting a care provider in moving the critical care bed and care cart from place to place, yet without violating the integrity of the footprint of the bed, as the motorized transport has the ability to nest within and dock with the hospital bed base underneath and within the footprint of the bed.

BRIEF DESCRIPTION OF THE DRAWINGS

FIG. 4 illustrates another embodiment of the ventilator cart of the present invention;

FIG. 5 is a view taken along line 5 of FIG. 4;

DESCRIPTION OF THE PREFERRED EMBODIMENTS

Figure 1:
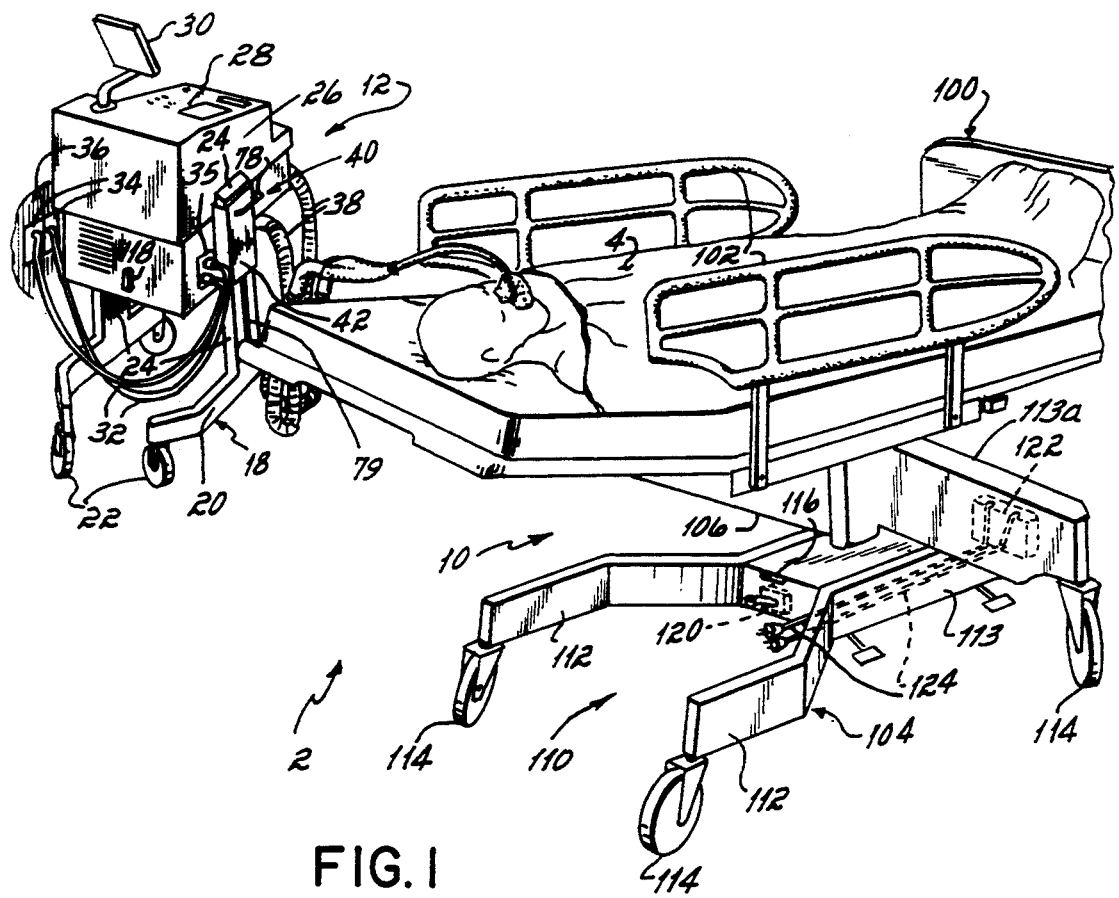
FIG. 1 is a perspective view of the present invention with the ventilator in its high position and separated from the hospital bed base and connected to AC wall outlets.
Figure 2:
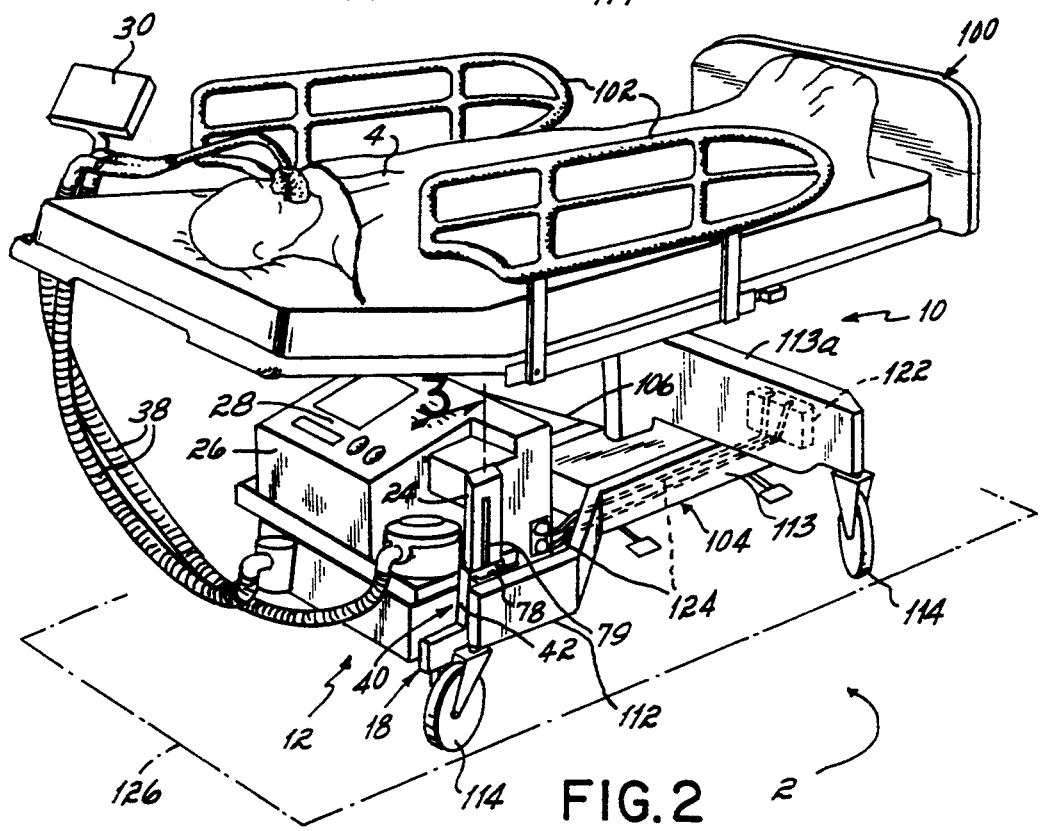
FIG. 2 is a view similar to FIG. 1 but illustrating the ventilator in its low position and docked to the hospital bed base and powered by the bed power supply.

With reference to the drawings, and first to FIGS. 1 and 2, there is illustrated a critical care environment designated generally by the numeral 2 for providing care to a critically ill patient 4. The standard critical care environment 2 includes, generally, a critical care bed assembly 10, and a mobile ventilator assembly 12. Other critical care equipment such as I.V. pumps, various monitors, and one or more terminals for entering patient care data, are also typically present in this environment but are not shown in the drawings for clarity purposes.

The mobile ventilator assembly 12 includes a ventilator cart 18 having a base 20 to which are mounted wheels or casters 22. Extending upwardly from the base 20 are a pair of uprights 24, 24 for supporting a ventilator 26. The ventilator 26 includes a control panel 28 and a flat panel display 30 for monitoring the ventilator 26. The ventilator 26 includes cables 32, 32 to supply power from suitable AC outlets 34, 34 mounted on a wall 36 of a critical care hospital room. The ventilator 26 is tethered to the patient 4 via hoses 38, 38.

Referring to FIG. 1, the ventilator 26 is illustrated in its upwardmost position where it is approximately beside height thereby facilitating operation of the ventilator 26 by a care provider by placing control panel 28 and display 30 at a convenient height.

Figure 3:
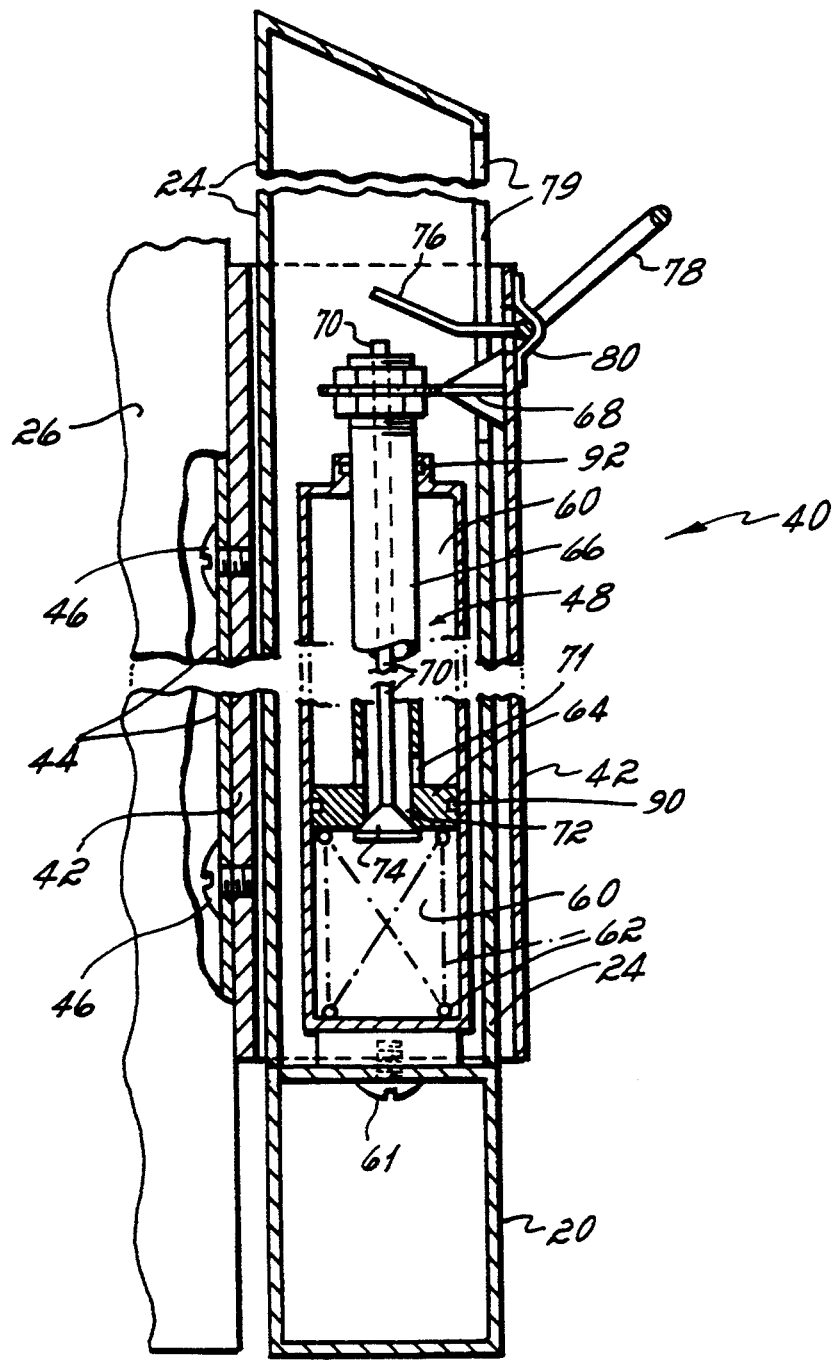
FIG. 3 is a schematic view taken along line 3 of FIG. 2 and illustrating one mechanism for raising and lowering the ventilator on the ventilator cart, the mechanism being shown in a lowered position.
Figure 6:
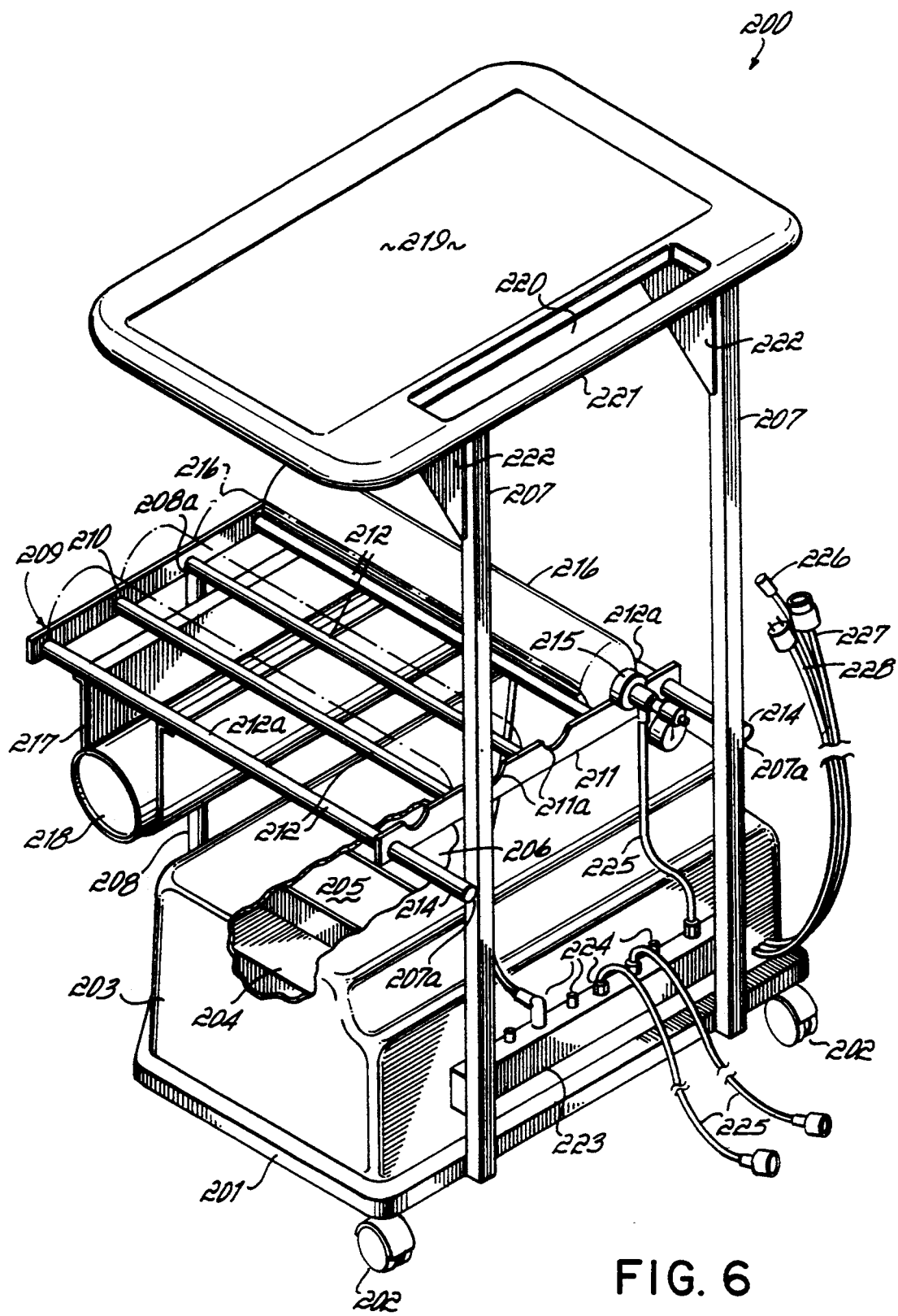
FIG. 6 is a perspective view of the care cart of the present invention.

With reference to FIG. 2, it will be noted that the ventilator 26 is lowered and positioned in a downwardmost compact configuration in order to be docked with the critical care bed assembly 10 for transporting both the bed assembly 10 and ventilator assembly 12 as a unit. In order to raise and lower the ventilator 26, each support 24 is provided with an adjusting mechanism 40 which allows for selectively raising and lowering the ventilator 26 on the supports 24. While most any suitable mechanism 40 could be utilized, one such adjusting mechanism 40 is illustrated in FIG. 3. Each mechanism 40 includes a generally box shaped sleeve 42 mounted for vertical sliding movement on its respective support 24. The sleeve 42 is fixedly secured to an external wall 44 of the ventilator 26 as by screws 46. Mounted internally of the support 24 is an air spring assembly 48. Air spring assembly 40 includes an elongated air tight plenum 60 fixedly secured by bolts 61 to the base 20 of cart 18. A coil spring 62 resides in the bottom of the plenum 60 and provides assistance in lifting the weight of the ventilator 26 when adjusting the ventilator from the low position to the high position. The coil spring 62 acts upon a block or piston 64 which is fixedly secured to the lower end of a hollow cylinder or piston rod 66. The upper end of cylinder 66 is connected to the sleeve 42 via a bracket 68. Contained within the cylinder 66 is a rod 70 which extends downwardly through an aperture 72 in the block 64 and has on its lower end a valve 74 which seats against the lower side of the block 64. The upper end of rod 70 is adapted to be moved vertically by a pivotable lever 76 which itself is an extension of a handle 78 mounted to sleeve 42 via a bracket 80. To facilitate this vertical movement of sleeve 42 and hence lever 76, the uprights 24 have a vertical slot 79 through which the bracket 68 extends. Block 64 includes around its periphery a suitable seal 90 to prevent air from transferring between the two cavities of plenum 60 defined by the block 64. A seal 92 is utilized at the upper end of plenum 60 to allow the cylinder 66 to travel vertically with respect to the plenum 60 without loss of air therefrom.

It will be appreciated that upward motion of handle 78 causes downward motion of lever 76, the end of which contacts the upper end of rod 70. Continued upward motion of handle 78 causes the lever 76 to force rod 70 downwardly causing valve 74 to unseat from the lower surface of block 64. Rod 70 is spring loaded with respect to cylinder 66 internally by means not shown, such that when handle 78 is released, lever 76 rises thereby releasing rod 70, which then returns to its normal state with valve 74 seated against the lower surface of block 64. The handle 78 may, if desired, also be spring biased to a released position shown but it is anticipated that the weight of handle 78 will overcome the weight of lever 76 and release itself by gravity.

When handle 78 is raised upwardly thereby depressing the upper end of rod 70 downwardly by virtue of the lever 76, it will be appreciated that air may freely travel through ports 71 in cylinder 66 and aperture 72 in block 64 to equalize the volume of air on both the upper and lower sides of the block 64. As handle 78 is additionally raised upwardly, sleeve 42 slides upwardly on post 24 and cylinder 70 and block 64 slide upwardly within plenum 60. Air volume is thereby equalized on either side of the block 64. When the ventilator 26 has been moved into its desired upward position, handle 78 is released, thereby causing valve 74 to reseat, the volume of air trapped therebelow by virtue of block 64 and seal 90 preventing the weight of the ventilator 26 from moving it downwardly. Of course, the force of coil spring 62 aids in overcoming the weight of the ventilator 26 when raising same, and must be overcome by downward force on the ventilator 26 when moving same downwardly.

Many other devices and mechanisms could similarly be employed to raise and lower the ventilator 26 on supports 24, and the invention is not limited to the specific embodiment illustrated, as same is only for illustrative purposes. Furthermore, such a device or mechanism could as easily be foot operated rather than hand operated.

Referring back now to FIGS. 1 and 2, the critical care bed assembly 10 includes a patient support surface or bed 100 with appropriate side guards 102, mounted onto a bed base 104 with suitable supporting structure 106, shown schematically. Bed base 104 includes a generally Y-shaped base frame 110 which includes outspread arms 112, 112 and a stem 113, and wheels or casters 114 mounted to the ends of the outspread arms 112, 112 and to a crosspiece 113a at the end of the stem 113. The outspread arms 112, 112 are adapted to receive the mobile ventilator assembly 12 therein, when the ventilator assembly is in its lowered compact configuration, as is illustrated in FIG. 1.

A suitable mechanical latch 116 is located generally within the trough area of the outspread arms 112, 112 and is employed for removably securing the mobile ventilator assembly 12 to the bed base 104. A suitable cooperating latch mechanism 118 is located on the rear side of the ventilator 26 in a suitable location to mate with bed latch 116 when the ventilator assembly 12 is at the lowered position of FIG. 2. While the cooperating latch 118 is illustrated as being mounted to a cross piece (not shown) of the ventilator 26, it could just as easily be mounted to a cross-piece (not shown) of the base 20 of the ventilator cart 18.

The bed 100 mounted to the bed base 104 generally includes suitable electrical controls for varying the height of the bed 100 above a floor surface by changing the attitude of the supporting structure 106. In order to prevent the bed 100 from being lowered onto the mobile ventilator assembly 12 when same is docked to the bed base 104, there is provided with the latch 116 a suitable switch 120 for disabling this high/low function of the bed 100. Most any suitable switch 120 could be utilized, and could be of, for example, the optical, mechanical or ribbon type.

To provide for uninterrupted operation of the ventilator 26, a suitable DC power supply 122 is provided. While the power supply 122 could be contained within the ventilator 26, mounted to the ventilator cart base 20, or could even be a part of the bed supporting structure 106, it is preferably mounted to the bed base 110. Suitable cables 124 connect the power supply 122 to the ventilator 26. Ideally, connecting cables 124 to the ventilator 26 would immediately internally to the ventilator 26 disconnect the AC power provided by the AC outlets 34 and immediately switch the ventilator over to DC power supplied by the power supply 122. Cables 32 could then be unplugged from their respective AC ventilator outlets 34 thereby providing for continuous operation of and elimination of any downtime associated with the ventilator 26 during transportation of the bed assembly 10 and ventilator assembly 12 to another location.

Referring to FIG. 2, it will be noted that the periphery of the bed 100 when projected downwardly onto the floor therebelow defines a footprint 126. As can be seen in the nested configuration, the mobile ventilator assembly 12 falls well within this footprint 126. Therefore, a hospital care provider normally adept at maneuvering the critical care bed assembly 10 need not have to account for a larger footprint in maneuvering the combination through doors, down aisles and into elevators. The care provider can simply maneuver the critical care bed assembly 10 as before, and without the necessity of individually rolling the mobile ventilator assembly 10 therebeside when transferring the equipment from one hospital room to another. Furthermore, the need to hurriedly transfer the equipment from one room to another and hence from one wall AC source to another wall AC source is eliminated.

Other variations of a combination hospital bed and ventilator are contemplated by the invention. For example, the ventilator could be separated from its wheeled cart and docked to the hospital bed base, to the supporting structure which mounts bed to base, or even the hospital bed itself underneath a head section thereof. All such variations would provide a hospital bed-ventilator combination, which combination is rollable as a single unit, with the ventilator being positioned within the footprint of the bed.

With reference to FIG. 4 there is illustrated a preferred embodiment of the ventilator cart of the present invention. The ventilator cart 150 includes an outermost rectangular base frame 151 which has sides 152, 153, 154 and 155. The cart 150 also includes an innermost rectangular support frame 156 which has sides 157, 158, 159 and 160. Innermost support frame 156 telescopes upwardly and downwardly with respect to the outermost base frame 151. The outermost frame 151 has fixedly secured thereto a pair of standards or uprights 161a and 161b, the lower ends of which are fixedly secured to frame sides 154 and 155, respectively. Fixedly secured to each standard 161a and 161b is a vertical slide 162, such as the type marketed under the trademark Accuride ®.

Referring to FIG. 5, it can be seen that each vertical slide 162 includes a plate 163 which is fixedly secured to a mounting block 164 via fasteners 165. Plate 163 includes a pair of inwardly facing legs 163a. Block 164 is secured to the upper end of each of the standards 161a and 161b. Vertical slide 162 further includes a rail 166 which is mounted for vertical translational movement with respect to the plate 163 via a number of steel balls 167 held within a vertically slidable ball retainer 179. A strap 178 encircles the vertical extent of the ball retainer 179, has ends fixed to the rail 166 at a point approximately midway of the vertical extent of the rail 166, and is secured to the plate 163 at 163b. Balls 167 in retainer 179 ride between the outer sides of the legs 163a of plate 163 and inwardly turned portions 166a of rail 166. It will be appreciated that legs 163a, balls 167 and inwardly turned portions 166a effectively function as a linear ball bearing assembly. Rail 166 is itself secured to mounting bar 168 which is, in turn, secured to a ventilator (phantom lines) via appropriate hardware 169.

At the upper end of each mounting bar 168 there is an ear 170 which is attached to the upper end of an air or gas spring 171. The lower end of each mounting bar 168 is fixedly secured to the sides 159, 160, respectively, of the frame 156. At the lower ends of each air spring 171 there is provided a clevis 172 which is secured to the piston 173 of the air spring 171. The clevis 172 is pinned via a pin 174 to an ear 175 one of which is located at each forward corner 176, 177 of the outermost frame 151. Legs 180 are provided for securing casters 181 to the outermost frame 151.

A ventilator (phantom) to be secured to the ventilator cart 150 rests atop the innermost support frame 156 and is secured to the mounting bars 168 via the fasteners 169. The angled orientation of the gas springs 171 allows for proper vertical travel of a ventilator supported by the cart 150, while simultaneously allowing one to physically overcome the force of the gas springs in order to force the ventilator downwardly into a nested configuration without any undue difficulty.

In order to actuate the gas springs 171 to raise the ventilator from its lowered position to its raised position, there are provided a pair of levers 185 located beneath the forward side 152 of the outermost frame 151. Each lever 185 includes a dog leg portion 186 which can be actuated by a foot of a care provider. Dog leg section 186 is connected to a linear section 187 which terminates in a hooked portion 188. Hooked portion 188 is positioned directly underneath the actuating rod 190 of the gas spring 171. The levers 185 are supported within tabs secured to the side 152, such as that shown at 192. Downward movement of the dog leg section 186 of each lever 185 causes upward rotation of the hooked portion 188, which actuates the actuating rod 190 of the air spring thereby enabling a care provider to manually raise the ventilator aided of course by the upward thrust of the gas spring 171.

It will be appreciated that the ventilator cart described herein can be used in any number of applications where a particular piece of medical equipment is desired to be rollably transported and selectively raised and lowered. Therefore, the cart is not to be limited solely for use in conjunction with ventilators and is claimed to have application to any number of different types of medical equipment.

With reference to FIGS. 6–11, and with like numbers representing like components, there is illustrated a care cart 200 for use in conjunction with the critical care bed 10 and mobile ventilator 12. The care cart 200 has a pentagonal base 201 with three casters 202 secured thereto for rolling the care cart 200 from place to place. A blow molded housing 203 is mounted atop the base 201 and houses one or more batteries 204, a battery charger 205 and a compressor 206. A pair of posts 207, 207 extend upwardly from the rear of the base 201, and a single post 208 extends upwardly from the front of the base 201 approximately half the vertical distance of the rear pair of posts 207, 207. A platform 209 is connected between the pair of posts 207, 207 and the single post 208 and is adapted to support four E-size oxygen and/or air tanks 216. The platform 209 has a transverse front support 210, a transverse rear support 211, and a plurality of longitudinal support rods 212 spanning between the front and rear supports 210 and 211, respectively. The rear ends 214 of the outwardmost longitudinal support rods 212a are secured to the rear pair of posts 207, 207 at 207a. Forward transverse support 210 is secured to the forwardmost vertical support 208 at 208a. The rearwardmost transverse support 211 includes semicircular notches 211a which receive the neck portions 215 of oxygen and/or air bottles 216. A semi-circular transverse support structure 217 is secured to the underneath side of the platform 209 for supporting a custom air tank 218 therein.

A shelf 219 projects forwardly from the upper ends of the pair of posts 207, 207. The shelf 219 includes a rectangular cutout 220 along its rear edge which forms a gripping bar 221 which can readily be grasped by a care provider for pushing the cart 200 from place to place. Gussets 222 are mounted between the shelf 219 and the pair of posts 207, 207 to provide additional rigidity for the shelf 219.

A manifold 223 is mounted near the lower ends of the pair of posts 207, 207. The manifold includes a plurality of connections 224 for connecting the air and oxygen bottles 216 thereto, as with supply lines 225. In order to supply the ventilator 12 of the present invention with DC electricity, air and oxygen from the care cart 200, supply lines 226, 227 and 228, respectively are provided for connecting to an electricity/air/oxygen controller box 240, which itself is connected to the ventilator 12 (FIG. 8), the operation of which will be subsequently described.

Figure 7:
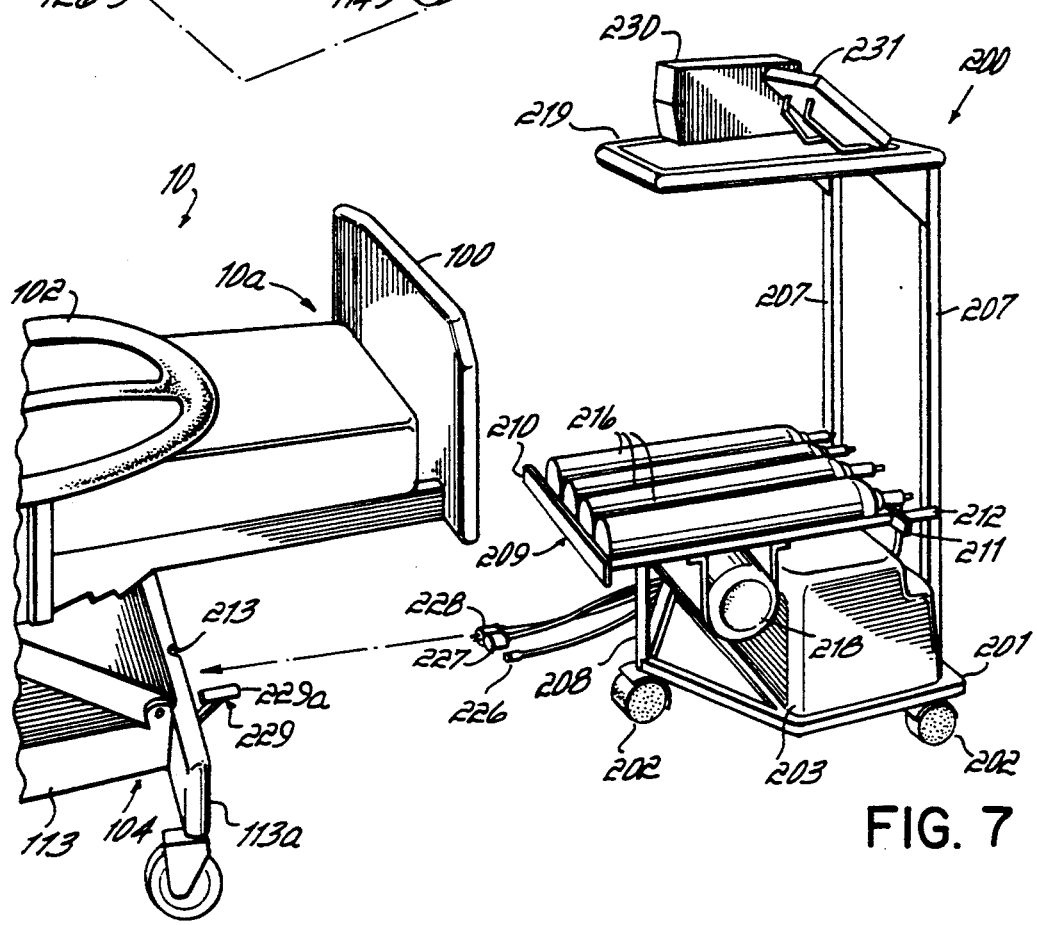
FIG. 7 is a perspective view of the care cart docking to a hospital bed.

With reference to FIG. 7, the care cart 200 is illustrated as approaching the critical care bed 10 for docking under a foot section thereof. On the crosspiece 113a of stem 113 there is pivoted a foot actuated lever 229 which is employed for latching the cart 200 to the bed 10. Upon docking the cart 200 with the bed 10 the forwardmost supporting post 208 enters into a concavedly cylindrical recess 213 in the crosspiece 113a. The lever 229 is then toggled upwardly as by a care provider's foot applying upward force to cross bar 229a, which upward toggling causes the lower end (not shown) of the lever 229 to pivot downwardly and rearwardly of the support post 208 thereby securing the support post 208 within the concavedly cylindrical recess 213 in the crosspiece 113a.

Numerous ancillary items can be employed with the care cart 200. For example, a drug box 230 can be incorporated on or into the shelf 219. A display monitor 231 can likewise be supported on the shelf 219 for displaying patient care data during transport of the patient on the bed 10 from one location to another.

Figure 8:
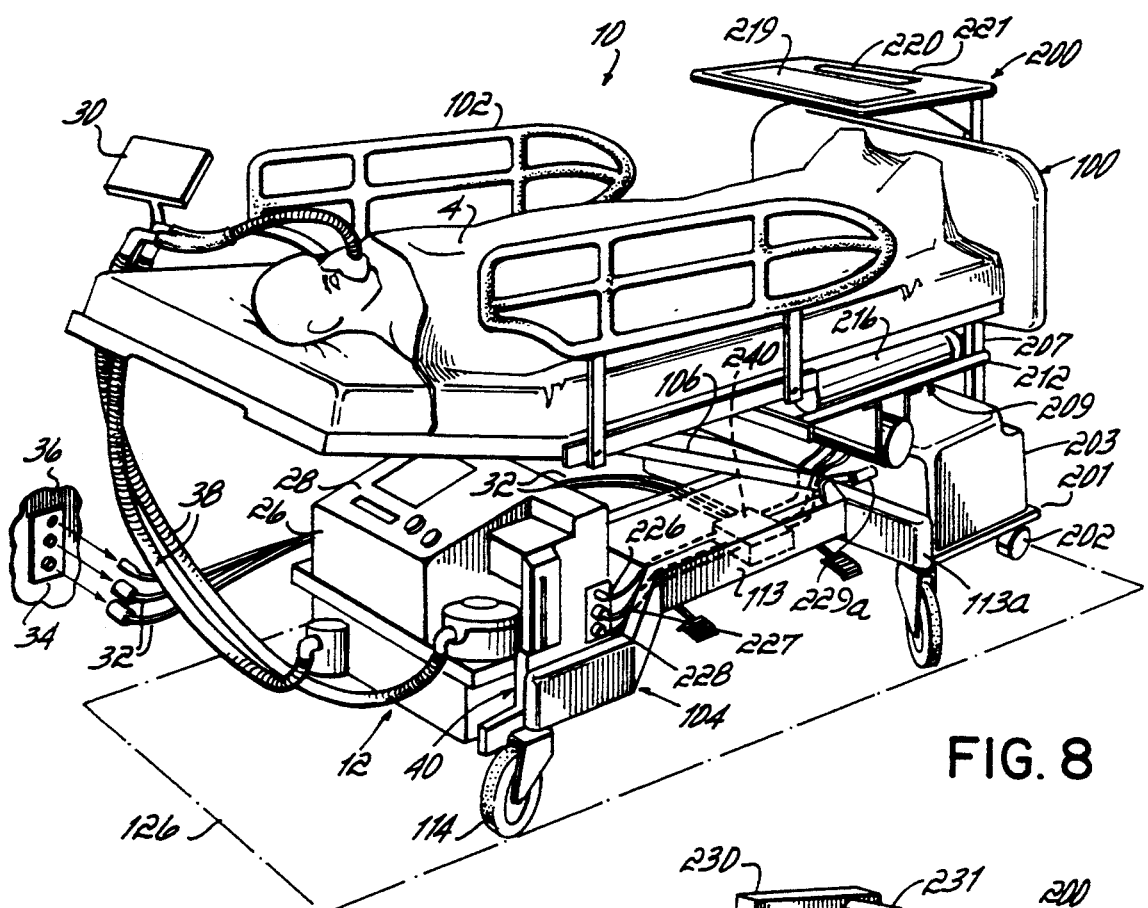
FIG. 8 is a perspective view of the care cart docked to a hospital bed.

With reference to FIG. 8, the care cart 200 is illustrated as being fully docked to the critical care bed 10, supplying ventilator 12 with DC electricity, oxygen and air during transport of the bed 10, ventilator 12 and cart 200. It will be seen that the ventilator 12 and cart 200 nestably fit within the mobile footprint 126 of the hospital bed 10. More particularly, and with respect to the care cart, it will be seen that platform 209 and shelf 219 are spaced apart vertically by a sufficient distance such that clearance is provided for footboard 100 on the bed 10. Therefore, when docked to the bed 10 (FIG. 8), platform 209 underlies the foot end 10a of the bed while shelf 219 overlies the foot end 10a of the bed 10. Further, it will be seen that stem 113 along with crosspiece 113a on bed base 104 are spaced a sufficient distance inwardly from the foot end 10a of the bed 10 to allow the base 201 and supporting platform 209 of cart 200 to completely come within footprint 126 of bed 10 (FIG. 8).

Figure 9:
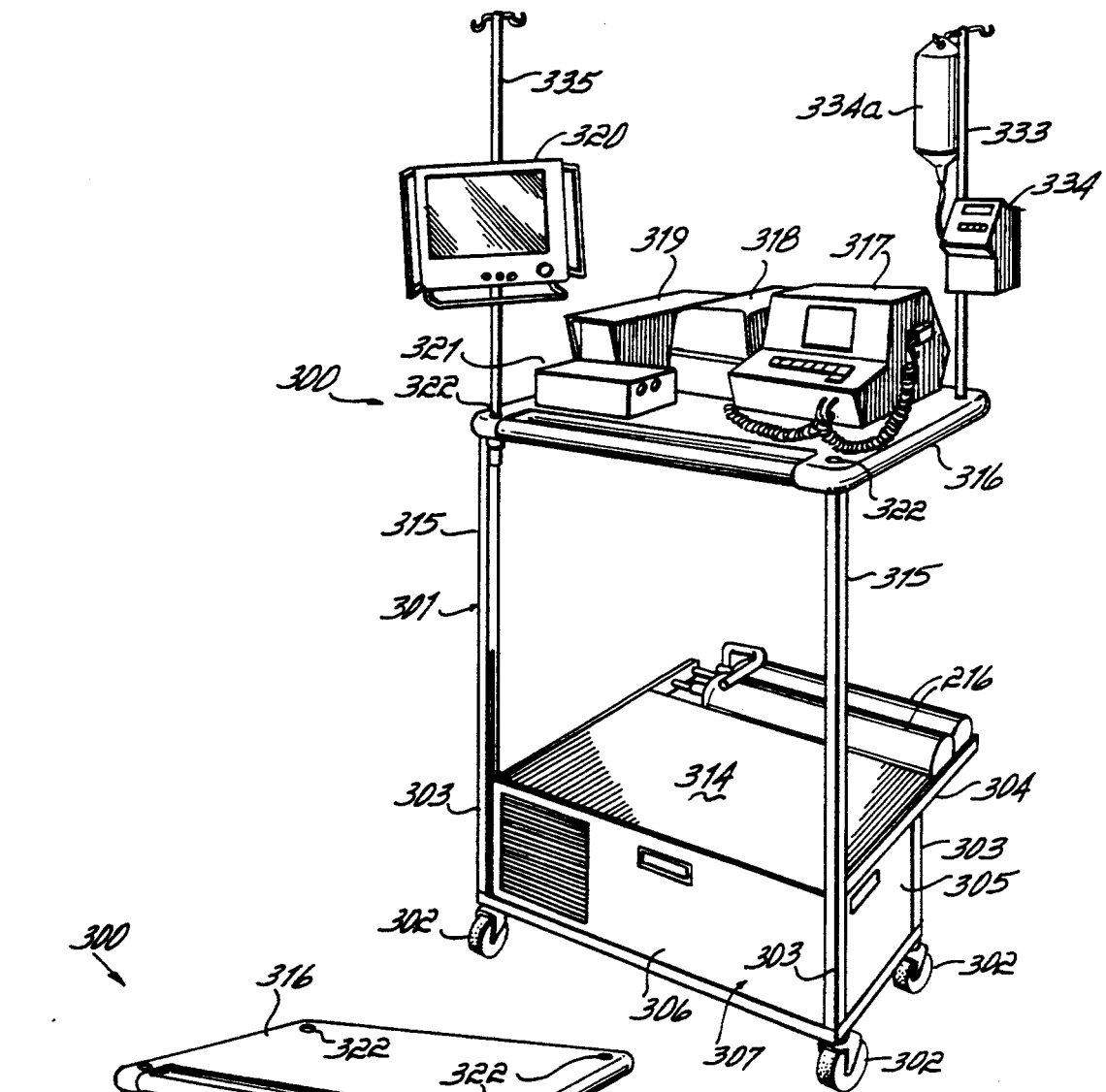
FIG. 9 is a perspective view of another embodiment of the care cart of the present invention.
Figure 10:
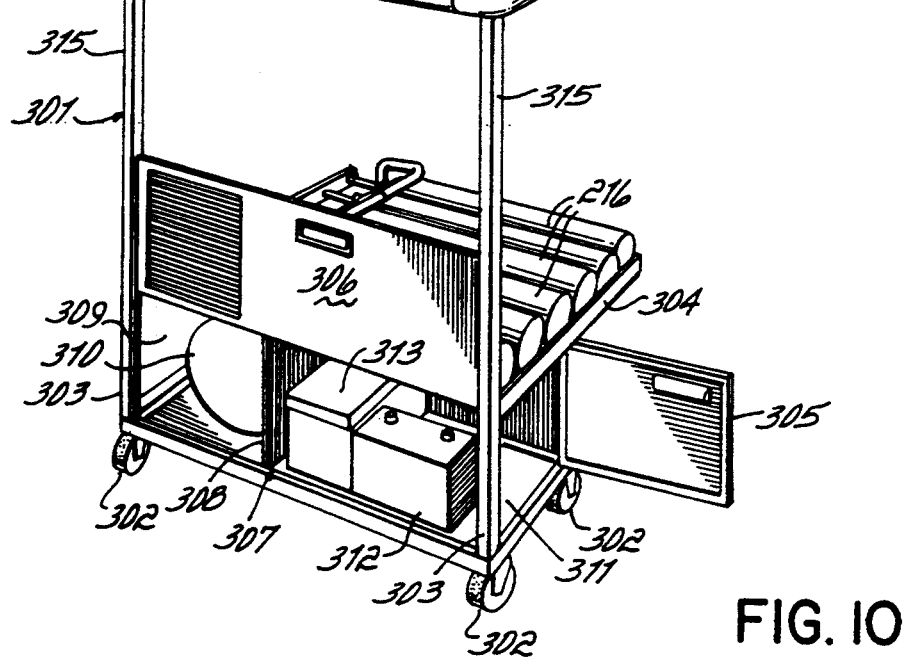
FIG. 10 is a perspective view of the care cart of FIG. 9 with doors opened and access cover removed.

Referring to FIGS. 9 and 10, there is illustrated another embodiment of the care cart designated by the numeral 300. The cart comprises generally a base 301 including casters 302, four housing corner supports 303 and a horizontal support frame 304 secured to the upper ends of corner supports 303. Base 301 and support frame 304 define a space which is enclosed with a pair of pivoting end doors 305, 305, an upwardly slidable, removable rear panel 306 and a forward panel (not shown). Side doors 305, rear panel 306 and the front panel are preferably of sheet metal fabrication. Side doors 305, rear panel 306, front panel, base 303 and supporting frame 304 define generally a housing 307 which includes an interior wall or divider 308 (FIG. 10) also of sheet metal construction. Divider 308 defines one compartment 309 which houses a liquid oxygen system 310 and another compartment 311 which houses batteries 312 and a battery recharger 313.

Supporting frame 304 includes provision for supporting six E-size oxygen and/or air tanks 126 thereatop (FIG. 10), or alternatively a removable shelf 314 (FIG. 9) can be snapped atop the frame 304 to provide additional shelf space in which case two E-size tanks 126 (FIG. 9) may still be supported atop the remaining portion of the supporting frame 304 which projects forwardly from underneath the shelf 314. A pair of uprights 315, 315 extend upwardly from the rear corner posts 303 of the housing and terminate in a forwardly projecting shelf 316, as in the prior embodiment.

Supported atop the supporting shelf 316 are a number of items employed in a critical care scenario, including a defibrillator 317, a drug box 318, a portable suction unit 319, and a transport monitor 320. Transport monitor 320 is powered by a tram 321 which, being a modular unit itself, is pluggable into a fixed monitor (not shown) in a typical critical care hospital room as part of, for example, a headwall unit or power column. The corners of the shelf 316 include I.V. pole sockets 322 therein such that I.V. poles 333 may be slipped therein, which support I.V. pumps 334 and I.V. solution bags 334a. Previously mentioned transport monitor 320 is likewise supported on a pole 335 which fits into one of the sockets 322 in the shelf 316.

In use, the care cart 200 or 300 of the present invention (the embodiment of either FIGS. 6–8 or FIGS. 9 and 10), is docked to the foot end 10a of a critical care hospital bed 10 and secured thereto with the foot actuated lever 229. The DC electricity, air and oxygen lines 226, 227 and 228 from the care cart are then connected to the electricity/air/oxygen controller box 240 which is itself connected to the ventilator 12 which is docked to the head end of the bed 10. This electricity/air/oxygen controller box 240 controls the flow of air, oxygen, DC power and AC power to the ventilator 12 from the head wall at the head of the bed 10 and the care cart 200 or 300 at the foot of the bed 10 during various stages of transport of the bed 10, ventilator 12 and cart 200 or 300. The controller box 240 is located on the bed base frame 110 adjacent the ventilator 12, and has three operating conditions or scenarios.

In the first condition, with the controller box being connected to oxygen and air at the wall, both oxygen and air are supplied to the controller box from the wall at 50 psi. With no care cart docked to the foot end of the bed, there is obviously 0 psi of oxygen and air supplied to the controller box from the foot of the bed. The controller box routes 50 psi oxygen and air to the ventilator.

In the second condition, again with the controller box connected to oxygen and air at the wall, wall oxygen and air are again supplied to the controller box at 50 psi. The care cart is now docked to the foot of the bed, supplying the controller box with 40 psi oxygen and air. With the bed in a stationary, semi-permanent position at the wall in the hospital room, the controller box closes the 40 psi oxygen and air supply from the cart at the foot of the bed and again routes 50 psi oxygen and air from the wall to the ventilator.

In the third condition, with the bed severed from its 50 psi wall oxygen and air during transport, the supply from the head end of the bed is 0 psi. With the care cart docked to the foot end of the bed during transport, and supplying 40 psi oxygen and air to the controller box, the box routes the 40 psi oxygen and air supply from the cart at the foot end of the bed to the ventilator, thereby supplying the ventilator with oxygen and air during transport.

The controller box further includes provision for routing AC and DC from the wall and care cart to the ventilator. When the bed is connected to AC at the wall, the box routes the AC to the ventilator which converts the AC to DC internally. When the bed is disconnected from AC at the wall, the box routes DC from the care cart to the ventilator.

After severing the bed from its AC electricity, oxygen and air supply at the wall, then, the bed, ventilator and care cart may thereafter be rolled about from place to place as a single unit by a care provider, normally by grasping the handhold built into the rear edge of the shelf of the care cart, the care cart providing total mobile support for the ventilator and bed, and hence patient 4.

Figure 11:
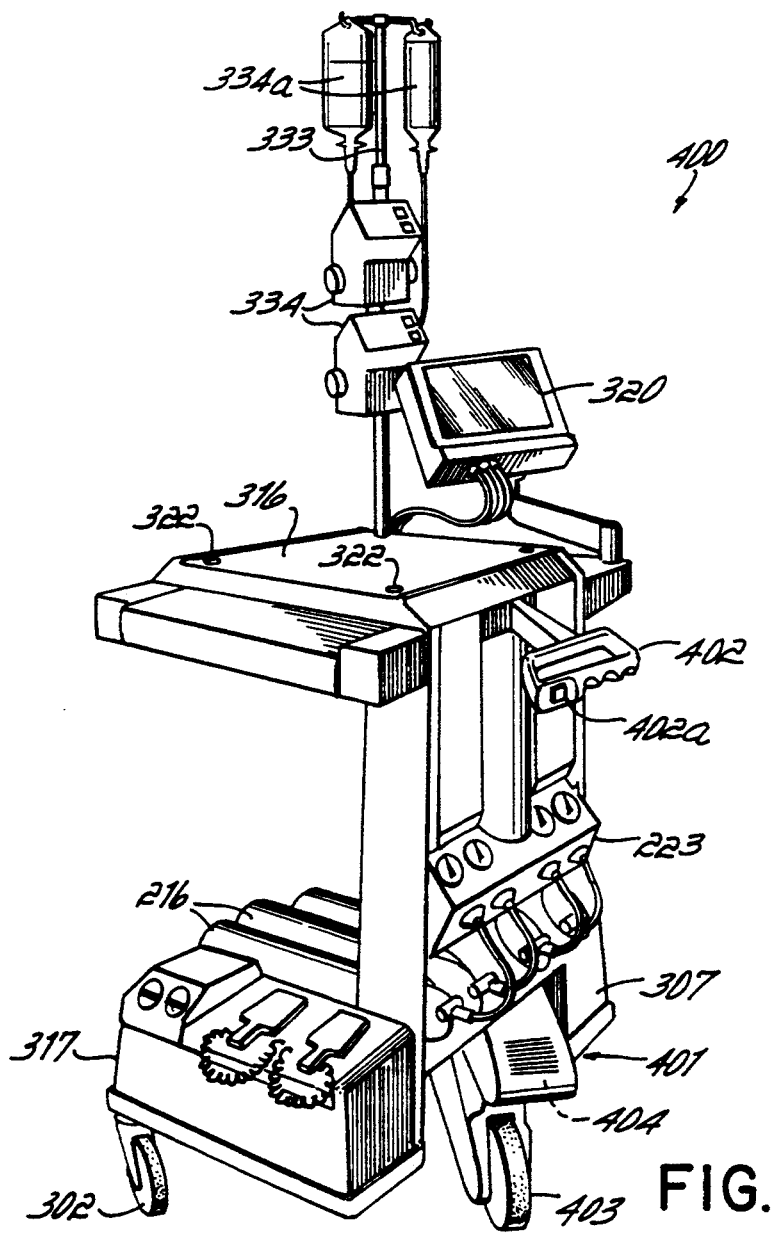
FIG. 11 is a perspective view of yet another embodiment of the care cart incorporating a motorized pilot jack therewith.

With reference to FIG. 11, and with like numbers representing like components, there is illustrated yet another embodiment of the care cart of the present invention designated generally by the numeral 400. In this embodiment, the cart includes all of the features of the former embodiments, with the additional feature of a motorized dolly or pilot jack 401 being included integrally with the care cart for motorized transport of the bed, ventilator and care cart. The pilot jack 401 includes a handle 402 which can be pivoted transversely with respect to the cart 400 for steering a drive wheel 403, which drive wheel is powered by a suitable motor 404. Pressing button 402a on handle 402 activates motor 404 driving wheel 403 in a forward direction. The motorized care cart 400 aids in overcoming the substantial increase in inertia generated by docking ventilator 12 and cart 400 to the bed 100. A suitable braking mechanism (not shown) would be incorporated within the cart 400 to aid in bringing the assembly to a stop. Preferably this pilot jack equipped care cart will be able to move 1500 lbs. of load and reach velocities up to 6 ft/sec. Preferably the pilot jack equipped care cart will have infinite variability in velocity control, including in both the forward and reverse directions. Preferably electrolyte deep discharge lead acid batteries will be used to power the pilot jack via a permanent magnet DC motor.

Other variations of the care cart are contemplated by the present invention. For example, other items can be incorporated into the cart in addition to those illustrated in the Figures, and in particular in FIG. 9. For example, a two-way communications system could be incorporated within the care cart for communications between the care provider transporting the patient atop the bed 10 and, for example, a care provider at the patient destination. Further, a lighting system could be incorporated into the care cart of the present invention to provide illumination for the care provider either for tasks to be performed on a patient or, for example, to light a hallway during transport of the patient atop the bed 10 during, for example, power outage. Furthermore, the care cart of the present invention could be adapted to support a miniaturized ventilator, known as a "transport vent".

The present invention has numerous advantages. A reduction in labor involved in preparing and transporting a critical care patient is effected. The total number of personnel required to transport a patient is reduced as well. The weight of the bed and the other devices utilized in conjunction with the bed is reduced which minimizes the physical effort expended by care providing personnel. The patient outcome is improved by giving the same care to the patient whether the patient is in the hospital room or in the hallway in transit between hospital rooms. And, all of the devices fit within the footprint of the bed to allow easy passage through doorways, around corners, and into elevators.

Figure 12:
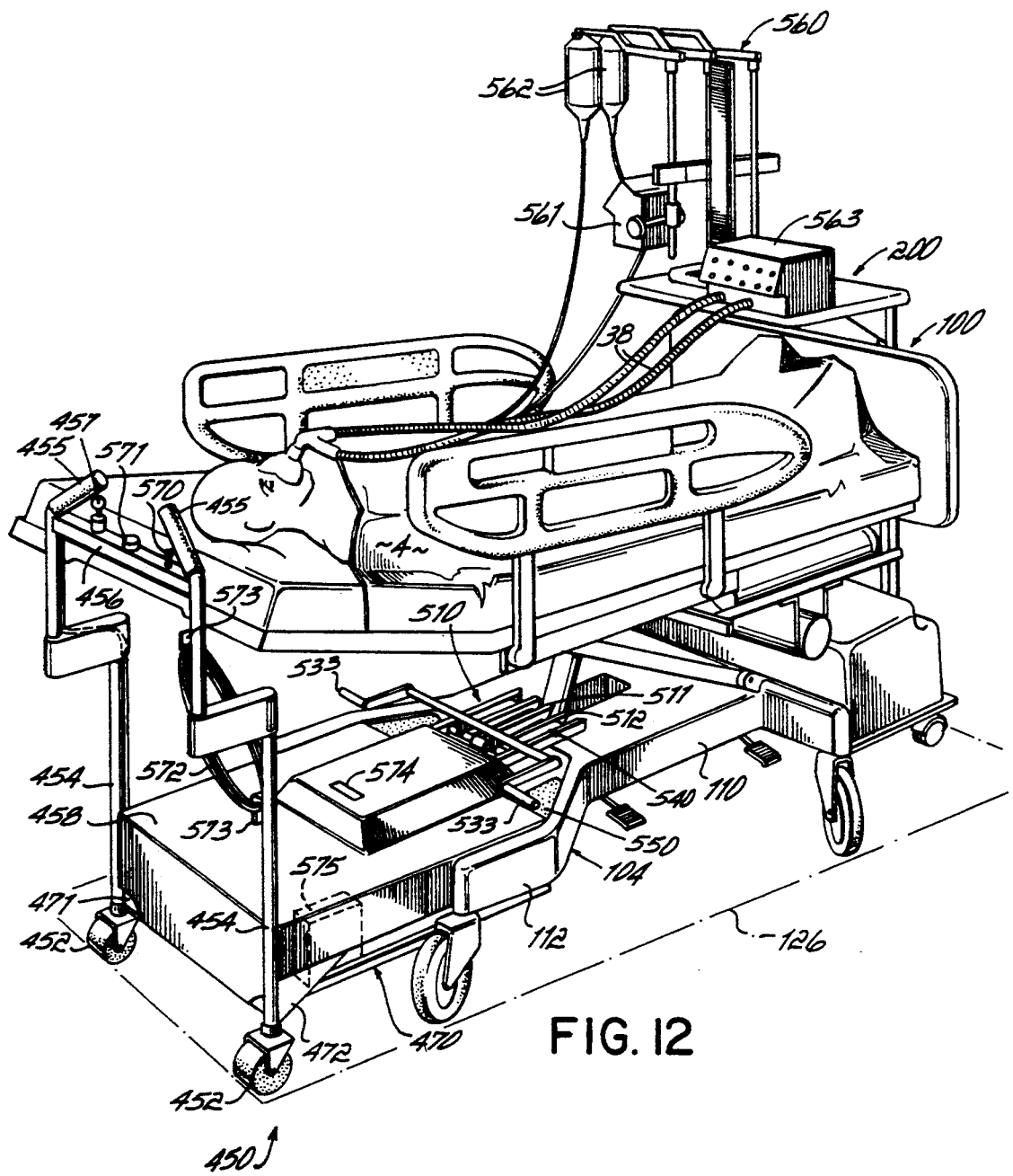
FIG. 12 is a perspective view of the motorized transport of the present invention docked to the head end of the hospital bed and with the care cart docked to the foot end of the hospital bed.

With reference to FIG. 12, and with like numbers representing like components, there is illustrated a motorized transport or "mule" 450 for motorized transport of the bed 100 with care cart 200 docked thereto. Mule 450 docks to the generally Y-shaped base frame 110 of the bed base 104 within and between the outspread arms 112, 112, the frame for which can be fabricated of welded steel tubing or by casting of an aluminum bronze alloy which is weldable to steel. When the bed 100 is used in conjunction with the mule 450, the mobile ventilator assembly 12 is replaced with a miniaturized transport vent 563 which is supported atop the care cart 200, for supplying patient 4 with oxygen and air during transport. Additionally, care cart 200 can be adapted to support an IV rack 560 which includes mounted thereto an IV pump 561 for pumping IV solution from IV bags 562. As used herein, "bed" and "hospital bed" are deemed to generically embrace all rollable patient supports, such as stretchers, birthing beds, critical care beds, etc.

More particularly, and referring to FIGS. 12-20, the mule 450 has a base 451 with a pair of casters 452, 452 mounted on its rear corners. At the front of the base 451 and centered transversely of the base, there is a non-marking rubber drive wheel 453. Drive wheel 453 is located at approximately the center-of-mass of the bed 100 and care cart 200 combination. By so locating drive wheel 453, the bed 100 and care cart 200 may readily be pivoted about the center-of-mass of the combination when maneuvering the combination, thus facilitating transport of the combination. Extending upwardly from the rear of the base 451 are a pair of handles 454, 454, the upper ends of each of which are outfitted with a hand grip 455 for gripping the handles 454, 454. Mounted on a transverse support 456 spanning between the handles 454, 454, is a joy stick 457 of the wiperless type for use in controlling the drive wheel 453. A cover 458 (FIG. 12) is removably secured atop the base 451, covering the components mounted thereon.

Figure 13:
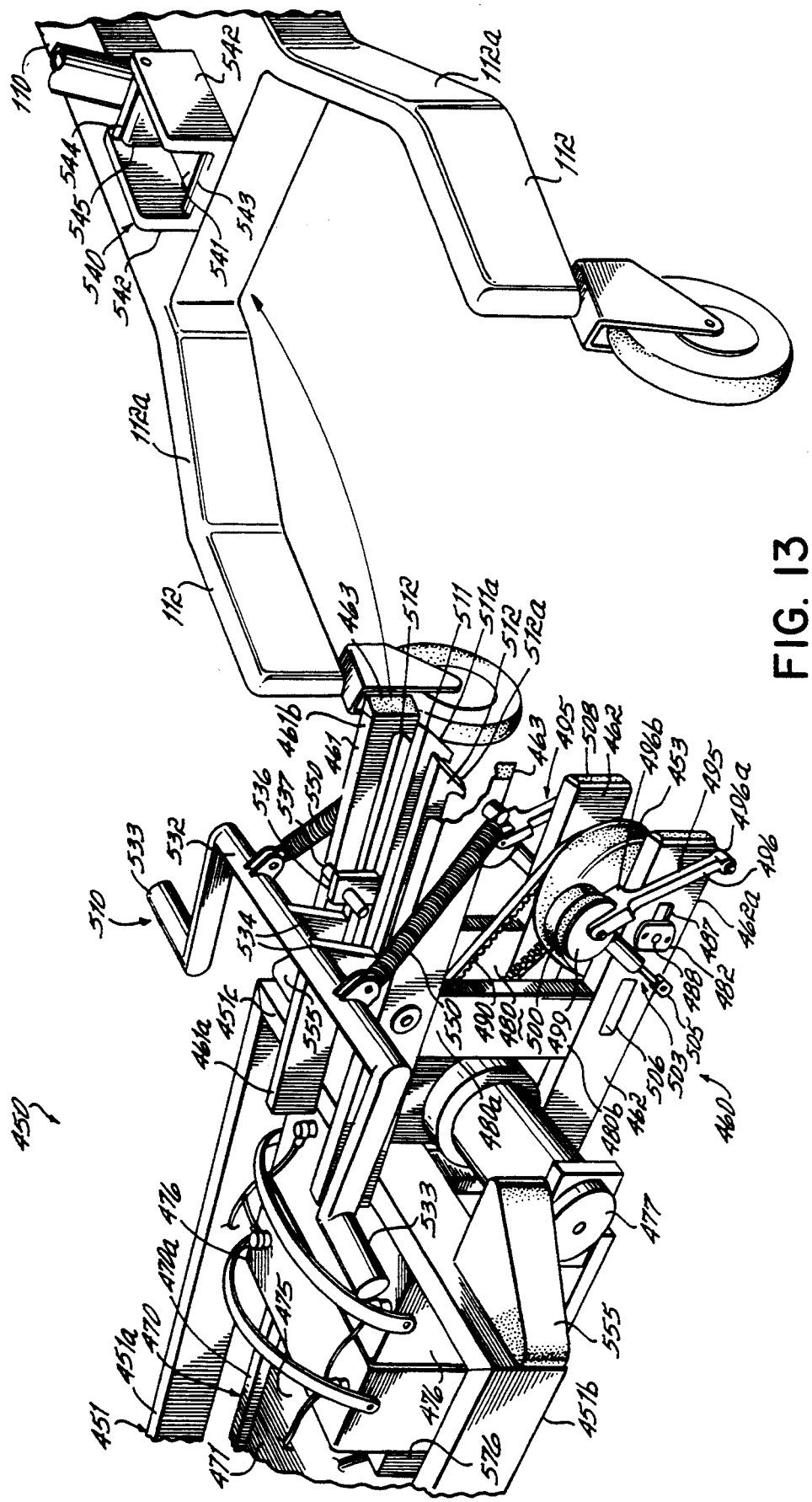
FIG. 13 is an enlarged, partial perspective view of the motorized transport approaching the y-shaped hospital bed base for docking thereto.
Figure 14:
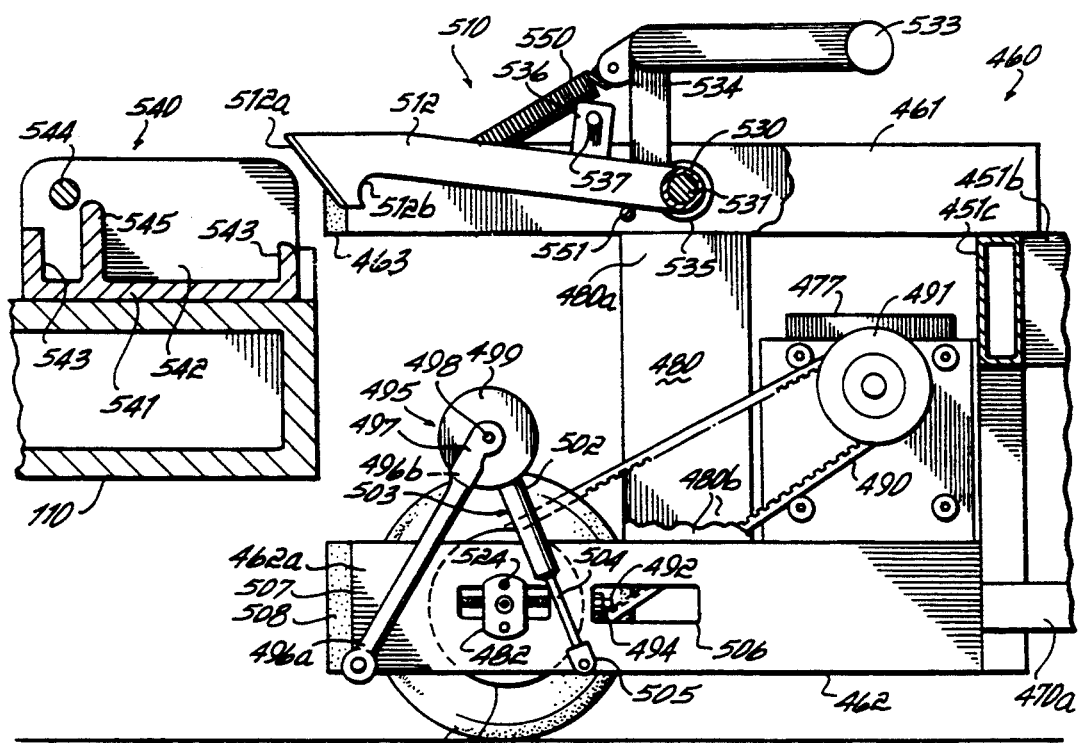
FIG. 14 is a partial side elevational view, in partial cross-section, of the motorized transport approaching the hospital bed base for docking thereto.
Figure 18:
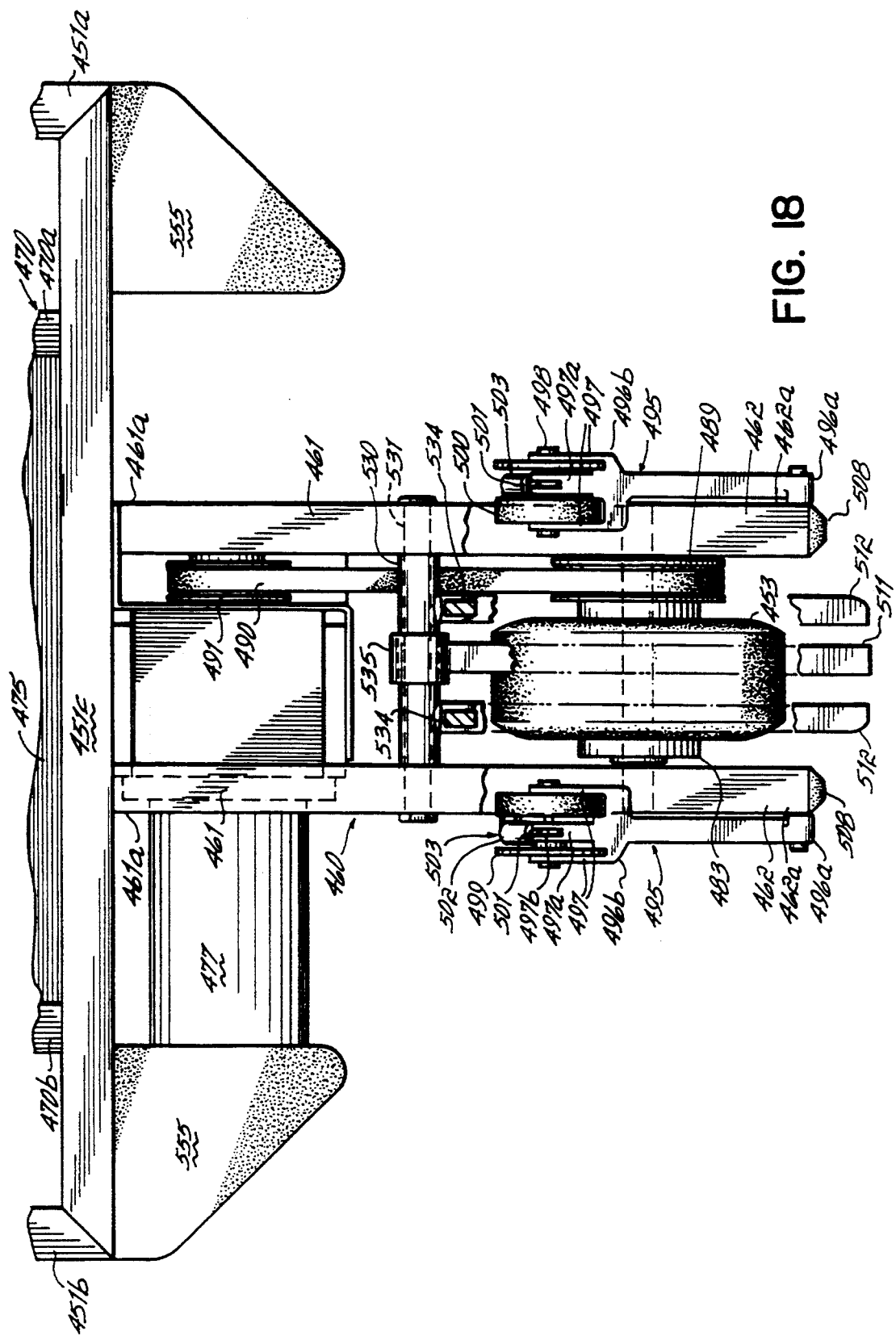
FIG. 18 is a top plan view of the front end of the motorized transport.
Figure 19:
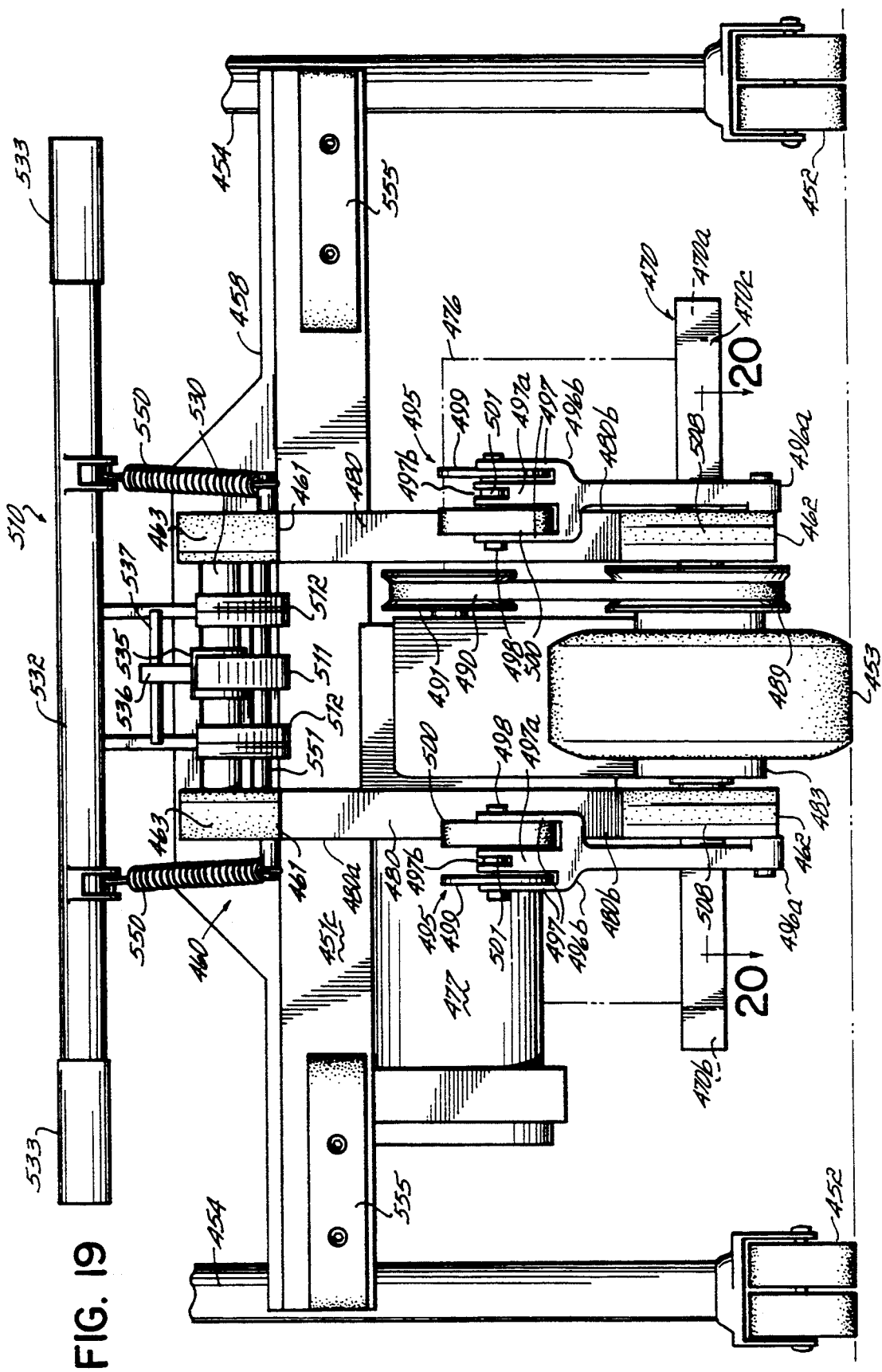
FIG. 19 is a partial front elevational view of the motorized transport.

Referring to FIGS. 13, 18 and 19, base 451 includes longitudinally oriented beams 451a and 451b which are fixedly secured together at their forwardmost ends by a transversely oriented beam 451c. Fixedly secured to the forward transverse beam 451c of base 451 is a drive wheel support structure designated generally by the numeral 460. Drive wheel support structure 460 includes an upper fork comprising a pair of supports 461, 461 and lower fork comprising a pair of supports 462, 462. The upper pair of supports 461, 461 have rear ends 461a, 461a which are fixedly secured to the upper edge of transverse support 451c of base 451. The forward ends 461b, 461b of support pair 461, 461 each include a nylon wedge 463 secured thereto, the necessity for which will be subsequently described.

Spaced underneath the supports 451a, 451b and 451c is a rectangular frame 470 having sides 470a and 470b which are fixedly secured at their forwardmost ends to forward transverse frame member 470c. The aft ends of the frame members 470a, 470b are fixedly secured to a rear transverse plate 471 (FIG. 12) which forms the rear edge of the base 451, the transverse edges of which are fixedly secured to the handles 454, 454. Gussets 472, 472 (FIG. 12) tie the rear ends of members 451a, 451b into the lower ends of the handles 454, 454 above the casters 452, 452. Fixedly secured to the underneath side of the frame 470 is a pan 475. Supported atop pan 475 and within base 451 are a pair of batteries 476, 476 which are employed to power a motor/gear box 477. The batteries 476, 476 are preferably of the sealed, deep cycling type, and the motor/gear box 477 is preferably of the permanent magnet motor, helical gear box type.

Drive wheel support structure 460 further includes a pair of vertical supports 480, 480 each of which has upper and lower ends 480a, 480b fixedly secured to a respective one of the upper and lower horizontal support pairs 461, 461 and 462, 462.

Referring to FIGS. 13 and 18-20, drive wheel 453 is rotatably supported on a shaft 485 the ends of which are supported in blocks 486, 486. The ends of shaft 485 pass through slots 487, 487 in the forward ends 462a, 462a of lower support pair 462, 462. A screw 488 secures an end cap 482 onto each end of shaft 485. A driven gear pulley 489 is 15 fixedly secured to a cast iron drive wheel hub 483 with screws 484 and is driven by a Poly Chain ® belt 490, which passes over drive pulley 491 which is fixedly connected to the output shaft of the motor/gear box 477. It will of course be appreciated that slots 487 in the supports 462, 462 allow fore and aft adjustment of drive wheel 453 in order to adjust tension in belt 490. Four allen head adjustment screws 492 adjust fore and aft travel of drive wheel 453, the bulkhead 493 in each of the support pairs 462, 462 being mateably threaded to accept a screw 492. Lock nuts 494 lock screws 492 against the bulkheads 493. The rearmost screws 492 and corresponding locknuts 494 are accessed through a slot 506 in each of the supports 462, 462, whereas the forwardmost screws 492 and corresponding locknuts 494 are accessed through an open forward end 507 in each of the supports 462, 462 by removing its respective nylon wedge 508.

On either side of drive wheel 453 there is a thrust washer 520, a needle type thrust bearing 521, another thrust washer 522 and a radial roller bearing 523. In order to load these components in compression to take the linear play out of these components along shaft 485, the end caps 482 are tightened onto the ends of the shaft 485. With blocks 486, 486 and hub 483 being slightly longer than the shaft 485, and as the caps 482 are tightened with screws 488, shaft 485 is placed in tension and the components on shaft 485 are placed in compression, thus removing any axial slop from the components on shaft 485. For adjusting shaft 485 between supports 462, 462, a pair of allen head screws 524 pass through one of the end caps 482 and bottom out against the side of the corresponding lower support 462. Advancing screws 524 inwardly removes any axial play of the shaft 585 from between the supports 462, 462.

Referring to FIGS. 13-19, on the outer side of each of the lower supports 462 there is a downward force generating mechanism 495 which, when the mule 450 is docked to the bed 100 generates a downward force on the drive wheel 453 to prevent the drive wheel 453 from slipping on a floor surface upon being rotationally accelerated by the motor/gear box 477. Each mechanism 495 includes an aluminum fork 496 which has a lower end 496a pivotally connected to the support 462. The upper end 496b includes a pair of spaced outside arms 497, 497, and a centermost arm 497a. A shaft 498 is fixedly secured to these arms 497, 497 and has rotatably supported thereon two wheels 499 and 500. Wheel 499 is essentially a relatively thin aluminum disk, whereas wheel 500 is a thicker nylon or glass filled nylon wheel. Pivotally supported to the shaft 498 between the wheels 499 and 500 and within slot 497b of center arm 497a is the upper end 501 of the cylinder portion 502 of a gas spring 503. Each gas spring 503 is preferably sized at 200 Newtons. The piston portion 504 of the gas spring 503 has its lower end 505 pivotally supported to the support 462. The distance between facing surfaces of the wheels 499 and 500 is sufficient to allow the upper end 501 of the cylinder portion 502 of the gas spring 503 to reside therein without coming into contact with or otherwise binding up against the inside surfaces of the wheels 499, 500 when the gas spring 503 is depressed.

Each of the mechanisms 495 generate downward force on the drive wheel 453 when the mule 450 is docked to the bed 100, as the wheels 499 and 500 of each of the mechanisms 495 roll underneath the bed base frame 110, the operation of which will be subsequently described in more detail.

Referring to FIGS. 13-19, a latching mechanism 510 is mounted on the drive wheel support structure 460 and is operable to latch the mule 450 to the bed base 110. The latch mechanism 510 includes three latch fingers: a centermost latch finger 511 and a pair of outer latch fingers 512, 512. Each of the three fingers 511 and 512, 512 includes upwardly ramped forwardly presenting surfaces 511a and 512a, 512a respectively, and radiused hook portions 511b and 512b, 512b respectively. The outer latch fingers 512, 512 are fixedly secured to a rotating sleeve 530 which rotates about a fixed shaft 531. A horizontally disposed bar 532 has rearwardly projecting handles 533. The bar 532 is rigidly connected to the rotating sleeve 530 by vertical links 534. The centermost latch finger 511 is itself rotatably connected to the rotating sleeve 530 with its own rotating sleeve 535. The centermost latch finger includes an upstanding tab 536 with a cross pin 537 press fitted therethrough.

Figure 15:
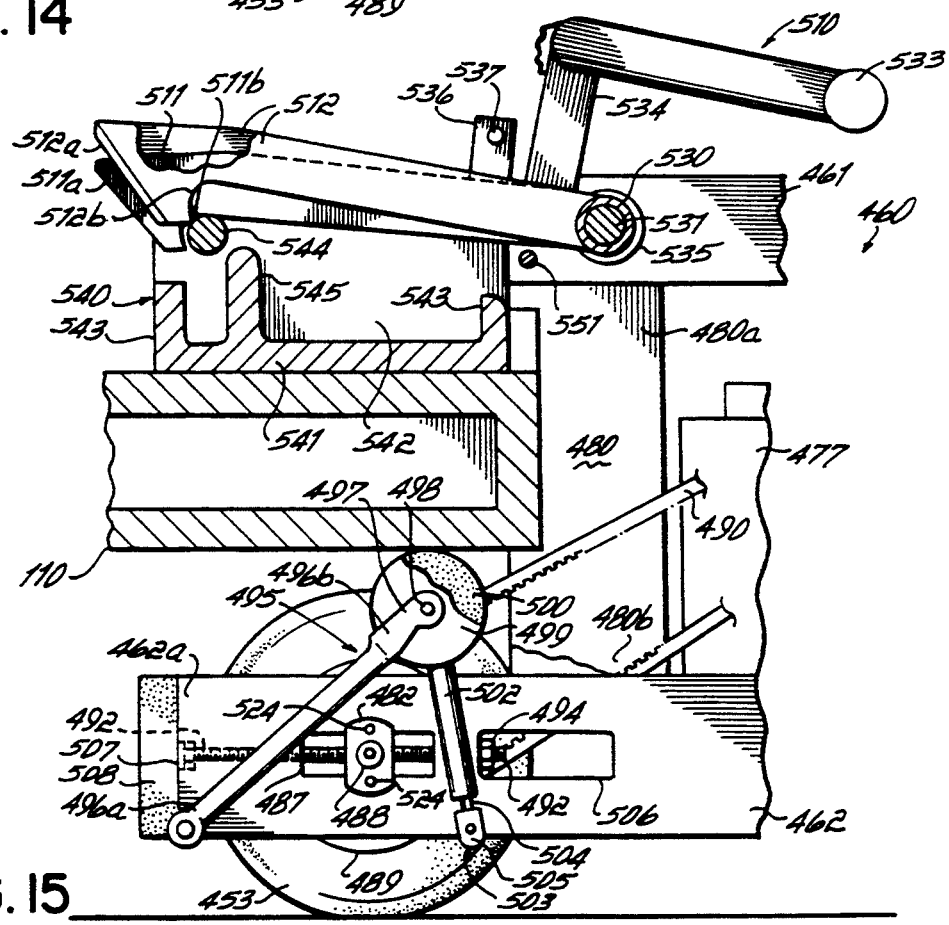
FIG. 15 is a partial side elevational view, in partial cross-section, of the motorized transport in the initial stage of docking to the hospital bed base.
Figure 16:
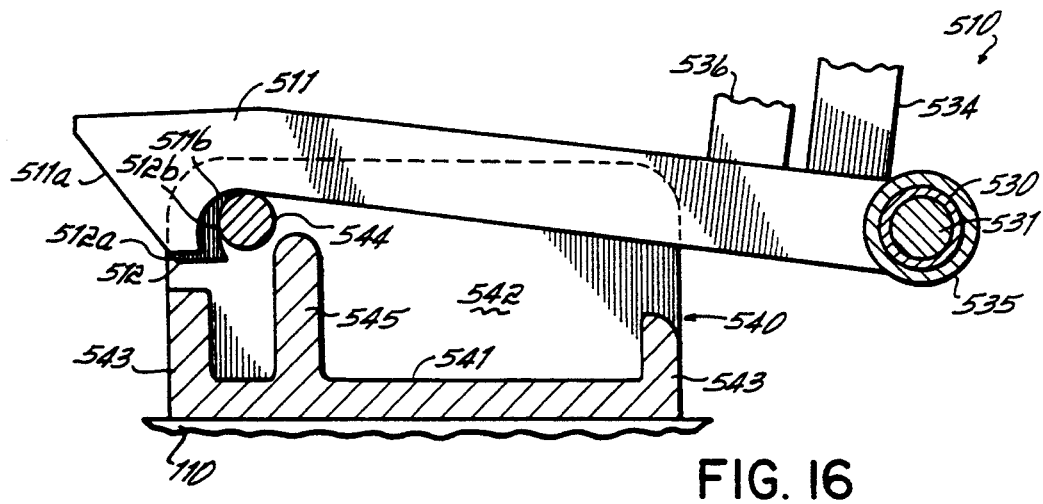
FIG. 16 is a partial side elevational view, in partial cross-section, of the latching fingers of the motorized transport latched to the hospital bed mounting block in the final stage of docking to the bed base.
Figure 17:
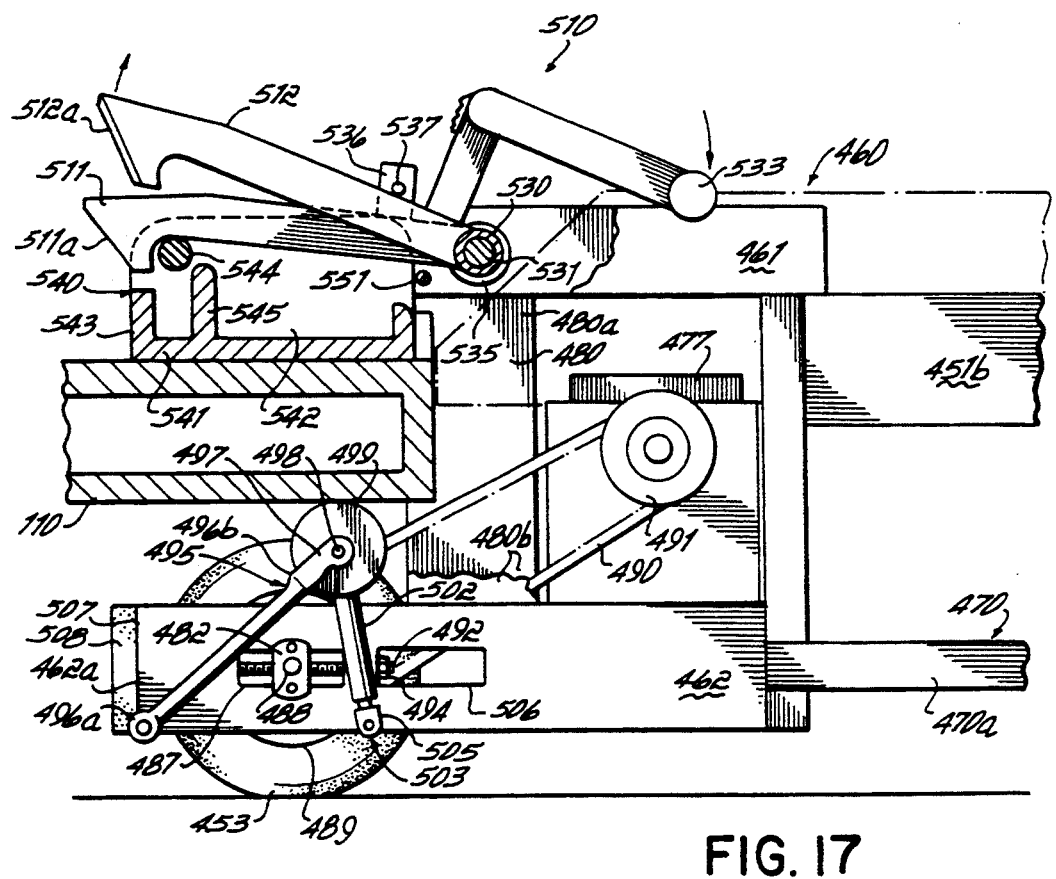
FIG. 17 is a partial side elevational view, in partial cross-section, of the motorized transport being released from the hospital bed base.

Referring to FIGS. 14-17, there will be seen a mounting block 540 for connection of the latching mechanism 510 thereto. The mounting block 540 is attached to the upper side of the bed base 104 at the base of the Y- shaped portion 110. The mounting block 540 essentially takes the form of a modified channel section having a bottom 541 and sides 542 and short end walls 543, 543. A bar 544 is press fitted into holes in the sides 542, 542 and is positioned near one end of the mounting block 540. Slightly forward of the bar 544 there is an intermediate transverse wall 545 having a height slightly less than the height of the cross bar 544. Wall 545 cooperates with the upwardly ramped forwardly presenting surfaces 511a and 512a, 512a of the centermost latch finger 511 and outer latch fingers 512, 512, respectively, such that forward movement of the mule 450 causes these upwardly ramped forwardly presenting surfaces 511a and 512a, 512a to ride up the wall 545 and to latch over the bar 544. Referring to FIGS. 15 and 16, it will be seen that the distance between the radiused hook portion 511b of the centermost latch finger 511 and the axis of rotation of the sleeve 530 is slightly greater than the distance between the hook portions 512b, 512b of the latch fingers 512, 512 and the axis of rotation of the sleeve 530. This allows the centermost latch finger 511 to initially latch the mule 450 to the bed 100, while further advancement of the mule 450 towards the bed 100 causes the outer latch fingers 512, 512 to then latch over the bar 544.

If the bed 100 is not loaded with a patient, the upwardly directed force of the gas springs 503, 503 acting upon bed base 110 can cause the bed base 110 to rise upwardly slightly. This slight upward movement of the bed base 110 requires a slightly longer latch finger, i.e., the centermost latch finger 511, to successfully latch the bed 100 to the mule 450, but when the bed is loaded up with a patient after the centermost latch finger 511 is latched over the bar 544 there is a slight amount of play between the bar 544 and the radiused hook portion 511b (FIG. 16). Accordingly, the outer latch fingers 512, 512 act as secondary latching devices such that all play is taken out of the connection between the mule 450 and the bed 100 after a patient is placed atop the bed 100 and thus loading the bed 100. In addition, the centermost latch finger 511 acts as a safety catch. This is because of the fact that when the rearwardly projecting handles 533 are depressed downwardly (FIG. 17) (either purposefully or inadvertently), thus pivoting the outer latch fingers 512, 512 off of the bar 544, there is a slight rotational delay between when these outer latch fingers 512, 512 disengage the bar 544 and when the centermost latch finger 511 disengages the latch bar, due to the cross pin 137 catching upon the upper surfaces of the outermost latch fingers 512, 512 at which time continued upward rotation of the outer latch fingers 512, 512 causes upward rotation of the centermost latch finger 511 and hence disconnection of the finger 511 from the crossbar 544.

To maintain the latching fingers 511 and 512, 512 in an approximately horizontally attitude, tension springs 550, 550 have upper ends connected to the crossbar 532 and lower ends indirectly connected to the upper fork supports 461, 461. A stop pin 551 is press fitted through the supports 461, 461 and serves to limit downward rotation of the latch fingers 511 and 512, 512, under the force of the springs 550, 550.

Figure 20:
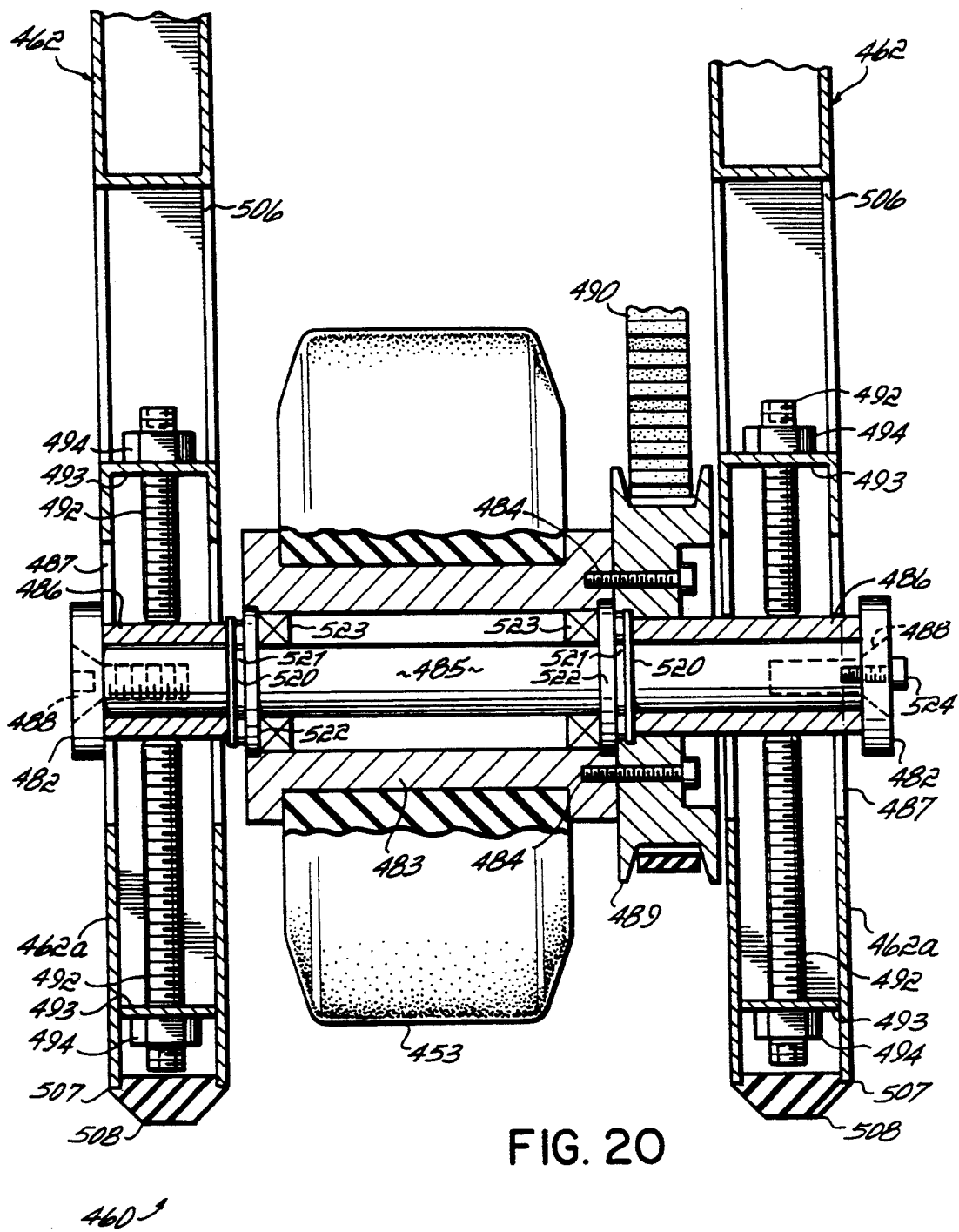
FIG. 20 is a view taken along line 20—20 of FIG. 19.

Referring to FIGS. 18 and 20, outwardly projecting nylon wedges 508, 508 inserted onto each end 461b of each support 461 guide the latching mechanism 510 onto the block 540, the wedges 508 directing the upper fork supports 461, 461 to the outer sides of the block 540. Initial entry of the mule 450 into the outspread arms 112, 112 of the bed base 110 is facilitated through the use of nylon shoulder wedges 555, 555, one of which is mounted at either end of the transversely oriented beam 451c of the mule base 451.

Referring back to FIG. 12, an on/off key 570 is provided for powering up the mule 450. An electronic fuel gauge 571 monitors the battery life in batteries 476, 476. The aforementioned joy stick control 457 is electrically connected to a pulse modulation controller circuit board 575 which is in turn electrically connected to the motor/gear box 477, and employs current pulsing technology to control the velocity of the motor 477 via the joy stick 457. A battery recharger 576 (FIG. 13) is included on board for recharging the batteries 476, 476. A cord 572 is electrically connected to the recharger 576 and is adapted to be connected to an AC wall outlet for charging the batteries. When not in use, the cord 572 is wrapped about a pair of cord holders 573, 573 which are attached to one of the handles 454, 454. An amp meter 574 is viewable through the cover 458 for monitoring charge of the batteries 476, 476 during recharging.

Mule 450 of the present invention could be utilized to move other objects in a hospital setting or otherwise as well. It could be used as a motorized transport for care carts, for example, or any other piece of medical equipment, or any rollable object, which has a base defining an opening into which the mule could dock. Accordingly, the mule invention is not to be limited only to motorized transport of hospital beds.

Those skilled in the art will readily recognize numerous adaptations and modifications which can be made to the present invention and which will result in an improved combination nestable mobile ventilator, critical care bed, nestable care cart and nestable motorized transport, yet all of which will be within the spirit and scope of the present invention as defined by the following claims. Accordingly, the invention is to be limited only by the appended claims and their equivalents.

What is claimed is:

1. Apparatus for powered transport of a hospital bed, the bed having a generally Y-shaped base with casters thereon, one end of which has a pair of spaced arms, comprising:

a base with casters thereon, said apparatus base being adapted to nest within the spaced arms of the Y-shaped hospital bed base and to dock thereto;

a drive wheel rotatably mounted on said apparatus base;

means mounted on said apparatus base for powering said drive wheel;

means mounted on said apparatus for controlling said drive wheel; and handle means connected to and extending upwardly from said apparatus base for steering said apparatus.

2. The apparatus of claim 1 wherein said means for powering said drive wheel is an electric motor.

3. The apparatus of claim 2 wherein said means for controlling said drive wheel is a pulse modulation controller electrically connected to said motor, and a potentiometer electrically connected to said pulse modulation controller.

4. The apparatus of claim 1 further including latch means for latching said apparatus to the hospital bed.

5. Apparatus for powered transport of a hospital bed, the bed having a generally Y-shaped base with casters thereon, one end of which has a pair of spaced arms, comprising:
  a base with casters thereon, said apparatus base being adapted to nest within the spaced arms of the Y-shaped hospital bed base and to dock thereto;
  a drive wheel rotatably mounted on said apparatus base;
  means mounted on said apparatus base for powering said drive wheel;
  means mounted on said apparatus for controlling said drive wheel;
  handle means connected to and extending upwardly from said apparatus base for steering said apparatus; and
  resilient means operable between said apparatus and the bed for exerting a downward force on said drive wheel to reduce a tendency of said drive wheel to slip on a floor surface.

6. The apparatus of claim 5 wherein said resilient means is a gas spring.

7. Apparatus for powered transport of a hospital bed, said apparatus being adapted to be docked to the bed at one end thereof and substantially within a footprint of the bed, said apparatus comprising:
  a base with casters thereon;
  a drive wheel rotatably mounted on said apparatus base;
  means mounted on said apparatus base for powering said drive wheel;
  means mounted on said apparatus for controlling said drive wheel;
  handle means connected to and extending upwardly from said apparatus base for steering said apparatus; and
  resilient means operable between said apparatus and the bed for exerting a downward force on said drive wheel to reduce a tendency of said drive wheel to slip on a floor surface.

8. The apparatus of claim 7 wherein said means for powering said drive wheel is an electric motor.

9. The apparatus of claim 8 wherein said means for controlling said drive wheel is a pulse modulation controller electrically connected to said motor, and a potentiometer electrically connected to said pulse modulation controller.

10. The apparatus of claim 7 further including latch means for latching said apparatus to the hospital bed.

11. The apparatus of claim 7 wherein said resilient means is a gas spring.

12. Apparatus for powered transport of a hospital bed, the bed having a base with casters, comprising:
  a base with casters thereon, said apparatus base being adapted to cooperate with the bed base and to dock thereto;
  a drive wheel rotatably mounted on said apparatus base;
  a power source mounted on said apparatus for powering said drive wheel;
  a controller mounted on said apparatus for controlling said drive wheel;
  handles connected to and extending upwardly from said apparatus base for steering said apparatus; and
  a resilient member operable between said apparatus and the bed for exerting a downward force on said drive wheel to reduce a tendency of said drive wheel to slip on a floor surface.

13. Apparatus comprising:
  A hospital bed comprising:
    a base with casters, said base being generally Y-shaped and having a stem portion and a pair of spaced arms extending from said stem portion, each said spaced arm having a laterally diverging portion and a longitudinal portion generally parallel a longitudinal axis of said stem portion, said laterally diverging portions having first ends connected to said stem portion and laterally spaced across its stem portion; and
  a motorized transport comprising:
    a base with casters on a rear end,
    a drive wheel rotatably mounted on a lower fork connected to said base, said lower fork positioning said drive wheel forwardly of and below said base,
    an upwardly projecting gas spring connected to said lower fork, said gas spring having a lower end pivotally connected to said fork and a roller rotatably mounted to an upper end of said gas spring, said upper end of said gas spring being pivotally connected to a first end of a link, said link having a second end pivotally connected to said fork,
    a motor mounted on said base for powering said drive wheel,
    handles extending upwardly from said base for steering said transport and bed,
    whereby said transport is adapted to dock between said spaced arms and to said stem, and to be removably secured thereat, said lower fork and drive wheel being positioned below said stem, and whereby said roller is forced downwardly against the resistance of said gas spring as said transport is docked to said bed base and as said roller rolls under said stem portion of said bed base, said gas spring developing a downward force on said drive wheel reducing a tendency of the drive wheel to slip on a floor surface.

14. Apparatus comprising:
  a hospital bed having first and second ends; and
  a motorized transport removably docked to and substantially within a footprint of said bed at one of said ends for assisting a care provider in rolling said bed from place to place;
  said bed having a generally Y-shaped base with casters thereon one end of which has a pair of spaced arms, said motorized transport comprising:
    a base with casters thereon, said transport base being adapted to nest within said spaced arms of said Y-shaped hospital bed base and to dock thereto;
    a drive wheel rotatably mounted on said transport base;
    means mounted on said transport base for powering said drive wheel;
    means mounted on said transport for controlling said drive wheel; and
    handle means connected to and extending upwardly from said transport base for steering said transport.

15. The apparatus of claim 14 wherein said means for powering said drive wheel is an electric motor.

16. The apparatus of claim 15 wherein said means for controlling said drive wheel is a pulse modulation controller electrically connected to said motor, and a potentiometer electrically connected to said pulse modulation controller.

17. The apparatus of claim 14 further including latch means for latching said motorized transport to said hospital bed.

18. Apparatus comprising:
a hospital bed having first and second ends; and
a motorized transport removably docked to and substantially within a footprint of said bed at one of said ends for assisting a care provider in rolling said bed from place to place;
said bed having a generally y-shaped base with casters thereon, one end of which has a pair of spaced arms, said motorized transport comprising:
a base with casters thereon, said transport base being adapted to nest within said spaced arms of said Y-shaped hospital bed base and to dock thereto;
a drive wheel rotatably mounted on said transport base;
means mounted on said transport base for powering said drive wheel;
means mounted on said transport for controlling said drive wheel;
handle means connected to and extending upwardly from said transport base; and
resilient means operable between said motorized transport and said bed for exerting a downward force on said drive wheel to reduce a tendency of said drive wheel to slip on a floor surface.

19. The apparatus of claim 18 wherein said resilient means is a gas spring.

20. Apparatus comprising:
a hospital bed having a base with casters thereon, said bed having first and second ends;
a piece of medical equipment having a base with casters thereon, said piece of medical equipment being removably docked to and substantially within a footprint of said bed at said first end, said piece of equipment including means for providing life support to a patient situated atop said bed; and
a motorized transport having a base with casters thereon, said transport being removably docked to and substantially within a footprint of said bed at said second end, said motorized transport for assisting a care provider in rolling said bed from place to place.

21. The apparatus of claim 20 wherein said bed has a generally Y-shaped base, one end of which has a pair of spaced arms, and wherein said motorized transport base is
adapted to nest within said spaced arms of said Y-shaped hospital bed base and to dock thereto, said motorized transport further comprising:
a drive wheel rotatably mounted on said transport base;
means mounted on said transport base for powering said drive wheel;
means mounted on said transport for controlling said drive wheel; and
handle means connected to and extending upwardly from said transport base for steering said transport.

22. The apparatus of claim 21 wherein said means for powering said drive wheel is an electric motor.

23. The apparatus of claim 22 wherein said means for controlling said drive wheel is a pulse modulation controller electrically connected to said motor, and a potentiometer electrically connected to said pulse modulation controller.

24. The apparatus of claim 21 further including resilient means operable between said motorized transport and said bed for exerting a downward force on said drive wheel to reduce a tendency of said drive wheel to slip on a floor surface.

25. The apparatus of claim 24 wherein said resilient means is a gas spring.

26. The apparatus of claim 21 further including latch means for latching said motorized transport to said hospital bed.

27. The apparatus of claim 20 wherein said piece of medical equipment including means for providing life support is a care cart comprising:
a support frame including said base;
a power supply mounted on said frame;
an oxygen supply mounted on said frame;
an air supply mounted on said frame; and
a ventilator mounted on said frame.

28. The apparatus of claim 27 further including a drug box mounted on said frame.

29. The apparatus of claim 27 further including a defibrillator mounted on said frame.

30. The apparatus of claim 27 further including a suction unit mounted on said frame.

31. The apparatus of claim 27 further including a battery charger mounted on said frame.

32. The apparatus of claim 27 further including an IV rack mounted on said frame.

33. The apparatus of claim 27 further including a transport monitor mounted on said frame.

34. A motorized transport for assisting a care provider in rolling a bed from place to place, comprising:
a base with casters on a rear end;
a drive wheel rotatably mounted on a lower fork connected to said base, said lower fork positioning said drive wheel forwardly of and below said base;
an upwardly projecting gas spring connected to said lower fork, said gas spring having a lower end pivotally connected to said fork and a roller rotatably mounted to an upper end of said gas spring, said upper end of said gas spring being pivotally connected to a first end of a link, said link having a second end pivotally connected to said fork;
a motor mounted on said base for powering said drive wheel; and
handles extending upwardly from said base for steering said transport and the bed;
whereby said transport is adapted to dock to a bed having a generally Y-shaped base having a stem portion and a pair of spaced arms extending from the stem portion, and to be removably secured thereat, said lower fork and drive wheel being adapted to be positioned below the stem, and whereby said roller is forced downwardly against the resistance of said gas spring as said transport is docked to the bed base and as sail roller rolls under the stem portion of the bed base, said gas spring developing a downward force on said drive wheel reducing a tendency of said drive wheel to slip on a floor surface.

35. Apparatus comprising:
a hospital bed comprising:
a base with casters, said base being generally Y-shaped and having a stem portion and a pair of spaced arms extending from said stem portion, each said spaced arm having a laterally diverging portion and a longitudinal portion generally parallel a longitudinal axis of said stem portion, said laterally diverging portions having first ends connected to said stem portion and laterally spaced across said stem portion, a latch bar mounted atop said stem portion between said laterally diverging portions of said spaced arms; and a motorized transport comprising:
- a base with casters on a rear end,
- a drive wheel rotatably mounted on a lower fork connected to said base, said lower fork positioning said drive wheel forwardly of and below said base,
- a latching finger pivotably mounted on an upper fork connected to said base, said upper fork positioning said latching finger forwardly of and above said base,
- a motor mounted on said base for powering said drive wheel,
- handles extending upwardly from said base for steering said transport and bed,
- whereby said transport is adapted to dock between said spaced arms and to said stem, and to be removably secured thereat, said upper fork being positioned above said stem, said lower fork being positioned below said stem, said pivoting latching finger latching over said latch bar, and said drive wheel being positioned beneath said stem.

36. Apparatus as in claim 35 further including:
an upturned channel section mounted on said stem, said channel section having sides, said latch bar being secured to said channel section sides; and wherein
said upper fork includes a forwardly and laterally outwardly tapering wedge on each forward end thereof, said wedges guiding said fork when said transport is being docked to said bed base so as to position said channel section between said fork and said latching finger between said channel section sides.

37. Apparatus as in claim 35 further including a forwardly and laterally inwardly tapering wedge attached to said motorized transport base on each forward corner thereof, said wedges guiding said transport when said transport is being docked to said bed base so as to position said transport base between said spaced arms.

38. Apparatus as in claim 35 wherein:
said latching finger is pivotably mounted on said upper fork for pivoting about a pivot axis, said latching finger extending forwardly of said pivot axis; and further including
a foot actuatable pedal operably connected to said latching finger and extending rearwardly of said pivot axis, said foot actuatable pedal being operable to pivot said latching finger out of engagement with said latch bar upon being depressed by a care provider.

39. Apparatus as in claim 35 further including:
an upwardly projecting gas spring connected to said lower fork, said gas spring having a lower end pivotally connected to said fork and a roller rotatably mounted to an upper end of said gas spring, said upper end of said gas spring being pivotally connected to a first end of a link, said link having a second end pivotally connected to said fork;
whereby said roller is forced downwardly against the resistance of said gas spring as said transport is docked to said bed base and as said roller rolls under said stem portion of said bed base, said gas spring developing a downward force on said drive wheel reducing a tendency of said drive wheel to slip on a floor surface.

40. A motorized transport for assisting a care provider in rolling a bed from place to place comprising:
a base with casters on a rear end;
a drive wheel rotatably mounted on a lower fork connected to said base, said lower fork positioning said drive wheel forwardly of and below said base;
a latching finger pivotably mounted on an upper fork connected to said base, said upper fork positioning said latching finger forwardly of and above said base;
a motor mounted on said base for power said drive wheel; and
handles extending upwardly from said base for steering said transport and a bed;
whereby said transport is adapted to dock to a bed having a generally Y-shaped base having a stem portion and a pair of spaced arms extending from the stem portion, and to be removably secured thereat, said upper fork adapted to be positioned above the stem, said lower fork adapted to be positioned below the stem, said pivoting latching finger adapted to latch to a latch bar mounted atop the stem, said drive wheel adapted to be positioned below the stem.

41. The motorized transport of claim 40 wherein said upper fork includes a forwardly and laterally outwardly tapering wedge on each forward end thereof, said wedges adapted to guide said fork when said transport is being docked to the bed base so as to position an upturned channel section having sides to which the latch bar is mounted between said fork and said latching finger between the channel section sides.

42. The motorized transport of claim 40 further including a forwardly and laterally inwardly tapering wedge attached to said motorized transport base on each forward corner thereof, said wedges guiding said transport when said transport is being docked to said bed base so as to position said transport base between said spaced arms.

43. The motorized transport of claim 40 wherein:
said latching finger is pivotably mounted on said upper fork for pivoting about a pivot axis, said latching finger extending forwardly of said pivot axis; and further including
a foot actuatable pedal operably connected to said latching finger and extending rearwardly of said pivot axis, said foot actuatable pedal being operable to pivot said latching finger out of engagement with the latch bar upon being depressed by a care provider.

44. The motorized transport of claim 40 further including:
an upwardly projecting gas spring connected to said lower fork, said gas spring having a lower end pivotally connected to said fork and a roller rotatably mounted to an upper end of said gas spring, said upper end of said gas spring being pivotally connected to a first end of a link, said link having a second end pivotally connected to said fork;
whereby said roller is forced downwardly against the resistance of said gas spring as said transport is docked to the bed base and as said roller rolls under the stem portion of the bed base, said gas spring developing a downward force on said drive wheel reducing a tendency of said drive wheel to slip on a floor surface.

45. Apparatus for powered transport of a hospital bed, the bed having a generally Y-shaped base with casters thereon, one end of which has a pair of spaced arms, comprising:
- a base with casters thereon, said apparatus base being adapted to nest within the spaced arms of the Y-shaped hospital bed base and to dock thereto;
- a drive wheel rotatably mounted on said apparatus base;
- a power source mounted on said apparatus for powering said drive wheel;
- a controller mounted on said apparatus for controlling said drive wheel; and
- handles connected to and extending upwardly from said apparatus base for steering said apparatus.

* * * * *